(12) United States Patent
Greener

(10) Patent No.: US 9,604,485 B2
(45) Date of Patent: Mar. 28, 2017

(54) COLOUR-FORMING MATERIALS, CONTACT RECORDING DEVICES AND PRESSURE RECORDING DEVICES

(71) Applicant: Active Device Development Limited, York, Yorkshire (GB)

(72) Inventor: Bryan Greener, York (GB)

(73) Assignee: Active Device Development Limited (GB)

( * ) Notice: Subject to any disclaimer, the term of this patent is extended or adjusted under 35 U.S.C. 154(b) by 0 days.

(21) Appl. No.: 14/442,917

(22) PCT Filed: Nov. 12, 2013

(86) PCT No.: PCT/GB2013/052983
§ 371 (c)(1),
(2) Date: May 14, 2015

(87) PCT Pub. No.: WO2014/076468
PCT Pub. Date: May 22, 2014

(65) Prior Publication Data
US 2015/0283839 A1    Oct. 8, 2015

(30) Foreign Application Priority Data

Nov. 14, 2012 (GB) .................................. 1220475.6
Jan. 17, 2013 (GB) .................................. 1300883.4
Mar. 15, 2013 (GB) .................................. 1304783.2

(51) Int. Cl.
*B41M 5/136*    (2006.01)
*B41M 5/155*    (2006.01)
(Continued)

(52) U.S. Cl.
CPC ........... *B41M 5/124* (2013.01); *A61B 5/1036* (2013.01); *A61B 5/447* (2013.01); *B41M 5/136* (2013.01);
(Continued)

(58) Field of Classification Search
CPC ........... B41M 5/136–5/155; G01L 1/24; A61B 5/1036
(Continued)

(56) References Cited

U.S. PATENT DOCUMENTS 4,447,075 A    5/1984    Miyamoto
6,066,329 A    5/2000    Morrison et al.
(Continued)

FOREIGN PATENT DOCUMENTS

EP    0005024 A1    10/1979
EP    0 593 060 A2    4/1994
(Continued)

OTHER PUBLICATIONS

PCT International Search Report for International Application No. PCT/GB2013/052983, dated Jan. 31, 2014, 4 pages.
(Continued)

*Primary Examiner* — Bruce H Hess
(74) *Attorney, Agent, or Firm* — Dorsey & Whitney LLP

(57) ABSTRACT

The present invention relates to devices and apparatus for detecting contact and optionally its duration and/or recording the level of pressure and/or its duration and/or recording the level of shear force and/or its duration. In particular, certain embodiments of the present invention relate to devices which comprise an element comprising a hydrophobic material and a color-forming material dispersed in at least a portion of the hydrophobic material. Certain embodiments of the present invention relates to materials comprising a solid dispersion of a color-forming material in an elastomeric hydrophobic material. The solid dispersion may take the form of a molecular dispersion or a partial molecular dispersion. Also included in the present invention, although not exclusively, are devices which comprise a hydrophobic material, a color-forming material and a color (Continued)

developing material wherein the color forming material and the color developing material are brought into contact when pressure of a predetermined threshold level is applied or removed from the device.

22 Claims, 34 Drawing Sheets

(51) Int. Cl.
- *G01L 1/24* (2006.01)
- *B41M 5/124* (2006.01)
- *B41M 5/145* (2006.01)
- *A61B 5/103* (2006.01)
- *A61B 5/00* (2006.01)

(52) U.S. Cl.
CPC .......... *B41M 5/1455* (2013.01); *B41M 5/155* (2013.01); *B41M 5/1555* (2013.01); *G01L 1/24* (2013.01)

(58) Field of Classification Search
USPC ................... 503/214, 226; 600/587; 116/206
See application file for complete search history.

(56) References Cited

U.S. PATENT DOCUMENTS

| | | | |
|---|---|---|---|
| 8,402,832 B2* | 3/2013 | Ribi | .......................... G01L 1/24 73/700 |
| 2004/0013839 A1 | 1/2004 | Ko et al. | |
| 2007/0207925 A1 | 9/2007 | Benkhoff et al. | |
| 2012/0109071 A1* | 5/2012 | Larsen | .................. A61J 7/0472 604/189 |

FOREIGN PATENT DOCUMENTS

| | | |
|---|---|---|
| EP | 0629511 A2 | 12/1994 |
| GB | 1426641 | 6/1976 |
| GB | 2 003 529 A | 3/1979 |
| JP | 08039928 A | 2/1996 |
| JP | 2007268914 A1 | 10/2007 |

OTHER PUBLICATIONS

PCT International Preliminary Report on Patentability for International Application No. PCT/GB2013/052983 dated May 19, 2015, 10 Pages.

\* cited by examiner

ZnAF-1 DA

COLOUR-FORMING MATERIALS, CONTACT RECORDING DEVICES AND PRESSURE RECORDING DEVICES This application is a national stage application under 35 U.S.C. §371 of International Application No. PCT/GB2013/052983, filed Nov. 12, 2013, entitled "Colour-Forming Materials, Contact Recording Devices and Pressure Recording Devices," which claims priority to United Kingdom Patent Application No. 1220475.6, filed Nov. 14, 2012, United Kingdom Patent Application No. 1300883.4, filed Jan. 17, 2013, and United Kingdom Patent Application No. 1304783.2, filed Mar. 15, 2013, the contents of all of which are hereby incorporated herein in their entirety by reference for all purposes.

FIELD OF THE INVENTION

The present invention relates to devices and apparatus for detecting contact and optionally its duration and/or recording the level of pressure and/or its duration. In particular, certain embodiments of the present invention relate to devices which comprise an element comprising a hydrophobic material and a colour-forming material dispersed in at least a portion of the hydrophobic material. Certain embodiments of the present invention relates to materials comprising a solid dispersion of a colour-forming material in an elastomeric hydrophobic material. The solid dispersion may take the form of a molecular dispersion or a partial molecular dispersion. Also included in the present invention, although not exclusively, are devices which comprise a hydrophobic material, a colour-forming material and a colour developing material wherein the colour forming material and the colour developing material are brought into contact when pressure of a predetermined threshold level is applied or removed from the device.

BACKGROUND TO THE INVENTION

Colour-formers are chemicals that can exist in two or more coloured states that can include a colourless state. The transition between coloured states is achieved by a change in the environment of the colour-former (CF). This change can, for example, be a change in pressure, temperature, light intensity or solvent. In each of these cases, the CF requires custom formulation with other excipients to respond to each specific environmental change. In general, different excipients are required to translate different environmental stimuli into a change in the coloured state of the CF; thus, the same CF can be employed in a range of colour-indicating applications for a variety of environmental changes.

For example, regarding the measurement of instantaneous pressure, Fuji Photo Film Co., Ltd. ("Fuji") produced a single-use pressure recording film, originally named Fuji Prescale Film. Fuji produced these pressure recording films in a range of grades (0.2-130 MPa). The basis of this product (for pressures in the range 0.2-50 MPa) is a pair of films; the first (named A-film) is coated with a layer of microspheres containing a colour-forming dye in its colourless state, the second (named C-film) is coated with a layer of a colour developer (CD). The colour developer converts the CF from a one coloured state (typically colourless) to another (typically coloured). The two films are stored separately to avoid accidental damage prior to use. During use, the two films are brought gently together with coated faces in contact. The application of a suitable localised force to the bilayer ruptures the microspheres containing the colour forming dye. The released dye contacts the colour developer and results in a localised strong colour that is visible through the transparent back of the film. This prior art is described further in UK Patent No. 1426641 and U.S. Pat. No. 4,447,075.

The pressure recording film described above is intended for the measurement of both momentary and continuous pressure distributions. According to user instructions, momentary pressure is recorded for 10 seconds and continuous pressure is recorded for 4 minutes. It is inherent in the construction of this pressure measurement system that the recording of cumulative, variable applied pressures over several hours or days is not possible.

Furthermore, the pressure recording film described above has a minimum pressure threshold of 0.2 MPa (1500 mmHg) and this threshold is significantly higher than the pressure range that is relevant for at least some applications of embodiments of the present invention as described below.

The low pressure threshold of existing electronic and non-electronic pressure-responsive arrays is dependent upon the mechanical properties of the materials from which these arrays are constructed.

An aim of certain embodiments of the present invention is to provide apparatus that enable the measurement of cumulative pressure.

An aim of certain embodiments of the present invention is to record pressures accumulated in the range of minutes to days within a total duration of hours to years.

An aim of certain embodiments of the present invention is to provide apparatus that enable the measurement of cumulative pressure with a response threshold in the range 0-1000 mmHg, e.g. 0-200 mmHg.

Certain embodiments of the present invention may have broad application in a range of fields requiring the passive recording of accumulated pressure including structural engineering, medical devices and sporting goods. For some of these applications, it may be desirable for the technology to be both robust and flexible.

SUMMARY OF CERTAIN EMBODIMENTS OF THE INVENTION

Certain embodiments of the present invention relate to the determination of at least one parameter, for example the application and/or duration and/or distribution of increased or reduced pressure and/or contact.

In order to create a cumulative pressure recording system, a system is provided that is able to record cumulative contact time. Certain embodiments of the present invention involve the use of a new material that delivers a colour-former to a colour developer in a time-dependent manner (e.g. over several minutes or hours or days) when components comprising the two materials are associated with one another.

In a first aspect of the present invention, there is provided a device for determining at least one parameter comprising an element comprising a hydrophobic material and a colour-forming material dispersed in at least a portion of the hydrophobic material.

Aptly, to achieve colour-indication, the colour-former or colour forming material (CF) interacts with a colour-developer or colour developing material (CD) and so both CF and CD are brought into communication. In one embodiment, the element comprising the hydrophobic material and the colour-forming material dispersed in at least a portion of the hydrophobic material is a first element and wherein the device comprises a second element, the second element comprising a colour developing material.

Aptly, the device comprises a single unitary component which comprises the first element and the second element.

Alternatively, the device comprises a first component comprising the first element and a second component comprising the second element, wherein the first component and the second component are separable. Aptly, the first component and the second component are brought into contact in use.

In one embodiment, the device comprises a third element located to maintain the first element and the second element in a non-associated state until pressure greater than or less than a predetermined threshold value is applied to the device.

Further details of the first, second and third elements of various aspects of the invention are provided herein.

Aptly, the parameter is the application of a predetermined level of pressure to the device or portion thereof. Aptly, the pressure may be an increased pressure level or alternatively a reduced pressure level, that is to say a pressure which is greater or less than a predetermined threshold value.

Aptly, the parameter is the application of reduced pressure to the device.

Aptly, the parameter is the application of increased pressure to the device. As used herein, the term "increased pressure" relates to a pressure value which is greater than the atmospheric pressure surrounding the device. The term "increased pressure threshold" refers to the pressure value threshold at which the device is able to indicate the increased pressure applied to it.

The increased pressure threshold may be in the range of between about 0 to 1000 mmHg e.g. 50 mmHg, 100 mmHg, 150 mmHg, 200 mmHg, 250 mmHg, 300 mmHg, 350 mmHg, 400 mmHg, 450 mmHg, 500 mmHg, 550 mmHg, 600 mmHg, 650 mmHg, 700 mmHg, 750 mmHg, 800 mmHg, 850 mmHg, 900 mmHg, 950 mmHg or 1000 mmHg.

As used herein, the term "decreased pressure" or "reduced pressure" relates to a pressure value which is lower than the atmospheric pressure surrounding the device. Aptly, the decreased pressure is referred to as "negative pressure" or "sub-atmospheric" pressure. The term "decreased pressure threshold" refers to the pressure value threshold at which the device is able to indicate the decreased pressure applied to it.

The decreased pressure threshold may be in the range of between about 0 to −1000 mmHg e.g. −50 mmHg, −100 mmHg, −150 mmHg, −200 mmHg, −250 mmHg, −300 mmHg, −350 mmHg, −400 mmHg, −450 mmHg, −500 mmHg, −550 mmHg, −600 mmHg, −650 mmHg, −700 mmHg, −750 mmHg, −800 mmHg, −850 mmHg, −900 mmHg, −950 mmHg or −1000 mmHg.

Aptly, the parameter is the duration of a predetermined level of pressure applied to the device or portion thereof. Aptly, the pressure may be an increased pressure level or a reduced pressure level. Aptly, the parameter is the application of reduced pressure to the device. Aptly, the parameter is the duration of application of increased pressure to the device.

Aptly, the parameter is the generation of contact with the device. Aptly, the parameter is the duration of contact with the device. Aptly, the duration of contact and/or pressure is continuous or intermittent e.g. non-continuous.

Aptly, the parameter is the distribution of application of a predetermined level of pressure to the device of portion thereof. Aptly, the parameter is the distribution of application of an increased pressure level to the device or portion thereof. Aptly, the parameter is the distribution of application of a reduced pressure level to the device or portion thereof.

Aptly, the parameter is the distribution of contact with the device of portion thereof.

In one embodiment, the parameter is application of a shear force to the device or portion thereof. The parameter may be the duration, strength and/or the direction of the shear force.

As described herein, certain embodiments of the present invention provide a solid elastomeric material in which is uniformly distributed one or more colour-forming materials, characterised in that the solid material allows the diffusion of the colour-forming material throughout its structure. Also included in certain embodiments of the present invention is an apparatus and/or a device comprising a solid elastomeric material and one or more colour-forming materials wherein the colour-forming material is substantially dispersed in the solid material and wherein the solid elastomeric material is capable of allowing diffusion of the colour-forming material through the solid elastomeric matter. The term "substantially dispersed" is used to indicate a solid dispersion of colour-forming material within a continuous phase of solid elastomeric material. The solid dispersion may be a molecular dispersion or a partial molecular dispersion, as shown in FIG. 31.

Aptly, the materials which allow the diffusion of colour-forming materials in the solid-state comprise a hydrophobic material.

In one embodiment, the solid elastomeric material is a hydrocarbon-based gel. One type of hydrophobic material includes material disclosed in U.S. Pat. No. 6,066,329 (Pennzoil Products Company). These materials are owned and marketed by Calumet Penreco Inc. under the trade name Versagel. These materials are elastomeric solids at 25° C. and pourable liquids at temperatures above 80° C. Materials of the Versagel C and Versagel R product ranges are all suitable for use as the hydrophobic material of the first aspect of this invention. The colour-forming material can be fully solubilised in the hydrocarbon gel at a temperature above the melting point of the hydrocarbon gel; cooling solidifies the gel.

In another embodiment, the hydrophobic material is a silicone based material. Silicone base materials are also suited to the uniform distribution of colour-forming materials throughout their structure because they are commonly prepared from two solvent-free liquid pre-polymers, in to either or both of which materials can be distributed. The inventor has identified that several colour-forming materials can be dissolved by one or both of these solvent-free liquid pre-polymers, enabling the uniform distribution of the colour-forming material in the final polymerised product at the molecular level. This may be desirable for the contact- or pressure-indicating application of these materials.

In one aspect of the present invention, there is provided a device comprising an element comprising a hydrophobic material and a colour-forming material dispersed in at least a portion of the hydrophobic material, wherein the element comprising the hydrophobic material and the colour-forming material dispersed in at least a portion of the hydrophobic material is a first element and wherein the device further comprises a second element, the second element comprising a colour developing material. The first element may be comprised in a first component of the device and the second element may be composed on a second component of the device, wherein the first component and the second component are brought into contact with each other during use.

When the two elements are brought together, colour-former molecules at the surface of the first element migrate to the second element and are transformed from a first coloured state (e.g. colourless) to a second coloured state (e.g. coloured). The second element may comprise a layer of solid colour-developer (for example Fuji Prescale C-film or the like).

Aptly, the second element comprises a colour-developer dispersed in a solid material. In the latter case, aptly, the solid material allows the diffusion of the colour-former through its structure.

Aptly, for contact time-dependent applications, the first and second element of the device allow diffusion of colour-former from the first element to the second element when they are in contact. Aptly, the first element and second element remain intact during the contact and non-contact motion. In one embodiment, the first element and second element are not adhesive for those applications requiring the measurement of repeated intermittent contact time. Thus, aptly, for applications involving intermittent contact, the first element and the second element are constructed of materials that allow repeated engagement and disengagement (i.e. are low- or substantially non-adhesive) and which enable the formation of a uniform and reproducible contact surface between the first element and second element (enabling the diffusion of the colour forming material across the element boundary).

Aptly, for pressure time-dependent applications, the first element and the second element are separated by a component that can be overcome by the application or removal of a force of greater than a predetermined threshold level.

Accordingly, in a further aspect of this invention, there is provided a device comprising a first element, a second element comprising a colour developer and a third element separating the first and second elements in the absence of a change (increase or decrease) in applied force.

In use, aptly, the first element is arranged at a controlled separation from the second element. This arrangement can be achieved by any means but may be achieved in a manner that modulates the distance of movement or the magnitude of applied pressure that is required to achieve direct contact of at least a portion of the first and second elements. Aptly, an apertured layer of controlled geometry can be interposed between the first and second element to achieve this purpose. In certain embodiments of the invention in which the first and second elements are flexible or deformable, the apertured layer may be relatively hard in comparison with the first and second elements e.g. have a Shore OO hardness greater than 80.

When the first element is separated from the second element (prior to or during use) no diffusion can occur between the first element and the second element and no colour development occurs. When the first element comes into contact with at least a portion of the second element (during use) the colour-former diffuses from the first element to the second element and the direct interaction of colour forming dye and colour-developer generates the coloured state of the colour former. Aptly, this arrangement records both the geometry and cumulative duration of the applied pressure.

Selection of the material properties of the first element and second element and the colour-forming dye and colour-developer may result in devices that can differentiate between applied pressure durations on the scale of minutes to days. Aptly, the rate of diffusion of the diffusible species e.g. the colour forming material from one element to the other dictates the rate of colour development. Aptly, the mechanical and geometrical properties of the first element and second element and the optional additional means of separation dictate the pressure-reporting threshold of operation of the device. In one embodiment, the material properties of the first element and second element are fixed and the device geometry and mechanical properties of the optional third element for separating these elements is adapted to allow for independent variation of pressure-threshold and pressure duration sensitivity in a given device.

In one embodiment, colour formation occurs substantially exclusively in or on the second element of the device and it occurs initially at the surface in contact with the first element. In embodiments in which neither the first element nor the second element is sufficiently transparent to enable this colour to be visible by eye or by electronic means, the elements are separated during use and directly observed on the contact face. Transparency is a function of material composition and material geometry. Aptly, for applications in which the separation of the device during use is undesirable (for example during uses requiring on-going observation of pressure accumulation and distribution), one or other or both of the first or second element is constructed of a material and geometry that allows colour development at the element interface to be directly observed without deconstructing the device.

In a further aspect of the present invention there is provided a process for the preparation of a material as described herein that comprises:
(a) uniformly dispersing a colour former in a pre-polymer liquid; and
(b) curing the pre-polymer liquid to a solid polymer.

In a yet further aspect of the present invention there is provided a process for the preparation of a device as described herein, the process comprising:
(a) uniformly dispersing a colour former in a polymer in its molten, liquid state; and
(b) cooling the polymer to its solid state.

In a further aspect of the present invention, there is provided apparatus for the measurement of cumulative contact duration and its distribution comprising a device as described herein and a calibrated colour chart to enable the determination of the cumulative duration of contact and its distribution.

In a further aspect of the present invention, there is provided apparatus for the measurement of cumulative applied pressure duration and its distribution comprising a device as described herein and a calibrated colour chart to enable the determination of the cumulative duration of applied pressure and its distribution.

In a further aspect of the present invention, there is provided apparatus for the measurement of cumulative applied shear and its distribution comprising a device as described herein and a calibrated colour chart to enable the determination of the cumulative duration of applied shear and its distribution.

In a further aspect of the present invention, there is provided a method of indicating cumulative application or removal of pressure, comprising locating a device as described herein in a target location and detecting a colour change of the device.

Aptly, the method is for detecting when a cumulative pressure applied to or removed from the device exceeds or falls below a predetermined threshold value. The predetermined threshold value may be from about 0 to about 1000 mmHg. Alternatively, the predetermined threshold value may be from about 0 to about −1000 mmHg.

In a further aspect of the present invention, there is provided a method of indicating cumulative application of shear, comprising locating a device as described herein in a target location and detecting a colour change of the device.

BRIEF DESCRIPTION OF THE DRAWINGS

The invention will now be described in more detail below, by way of example only, with reference to the accompanying drawings, in which:

FIG. 3 is a schematic figure and the relative dimensions of the components are not drawn to scale or relative to one another. In particular, the colour-forming material (20) may be dispersed at the molecular scale in certain embodiments of the invention.

FIG. 4 is a schematic figure and the relative dimensions of the components are not drawn to scale or relative to one another. In particular, the colour-forming material (201) may be dispersed at the molecular scale in preferred embodiments of this invention;

FIG. 5A shows a device (100) comprising a first element (101) in which is dispersed a colour-forming dye in its colourless state (201), and a second element (301) in which is immobilised a particulate colour developer (401), characterised in that both the first element and second element are constructed of a solid material that allows the diffusion of the colour-forming dye but not the colour developer;

In FIG. 5B, the first element (101) and the second element (301) have been brought into contact by an external stimulus and the colour-forming dye (201) has begun to diffuse from the first element (101) into the second element (301). Some of the colour-forming dye that has entered the second element (201) has yet to encounter a colour developer particle, while the majority of the colour-forming dye that has entered the second element has encountered a colour developer particle and has generated an irreversible and highly coloured complex (220). In FIG. 5C this process has continued as contact time advances. The elements are then separated once more, arresting the state of colour development, as shown in FIG. 5D;

FIG. 6A shows a device (100) comprising a first element (101) in which is dispersed a colour-forming dye in its colourless state (201), and a second element (301) in which is immobilised a particulate colour developer (401) and associated with which is a third element (310). Aptly, the first, second and third element are constructed of a solid material that allows the diffusion of the colour-forming dye but not the colour developer;

In FIG. 6B, the first element (101) and the third element (310) have been brought into contact by an external stimulus e.g. application of a pressure above or below a predetermined threshold value. FIG. 6C illustrates that the colour-forming dye (201) has begun to diffuse from the first element (101) into the third element (310). No colour is developed in the second element (301) while the colour-former is diffusing across the third element (310). In FIG. 6D, some of the colour-forming dye has entered the second element (301) and has yet to encounter a colour developer particle (201), while the majority of the colour-forming dye that has entered the second element has encountered a colour developer particle and has generated an irreversible and highly coloured complex (220). The geometry and composition of the third element (310) dictate the delay time before colour is formed in the second element (301) after contact between the separate elements;

FIG. 7A illustrates a device (100) comprising a first element (101) in which is dispersed a colour-forming dye in its uncoloured state (201), a second element (301) in which is immobilised a particulate colour developer (401), and a third element (501) containing apertures (550) separating the first and second elements in the absence of applied pressure, characterised in that both the first element and second element are constructed of a solid material that allows the diffusion of the colour-forming dye but not the colour developer. FIG. 7B illustrates that when topical pressure (1000) is applied to the device, the first and/or second elements of the device are distorted through the apertures (550) of the third element (501) and contact one another (601);

In FIG. 7C, the colour-forming dye (201) has begun to diffuse from the first element (101) into the second element (301). Some of the colour-forming dye that has entered the second element (210) has yet to encounter a colour developer particle, while the majority of the colour-forming dye that has entered the second element has encountered a colour developer particle and has generated an irreversible and highly coloured complex (220). In FIG. 7D this process has continued as contact time advances. The topical pressure is removed and the elements are then separate once more, arresting the state of colour development, as shown in FIG. 7E;

In FIG. 8A, the device (100) comprises a pair of dissimilar layers (101) and (1010) each comprising a colour forming material on either side of a layer (301) comprising a colour developing material. Each layer is separated by a dissimilar third element which acts as a spacer layer, (5010) and (5011), of dissimilar geometries (e.g. yarn diameter, aperture size);

Figure 7:
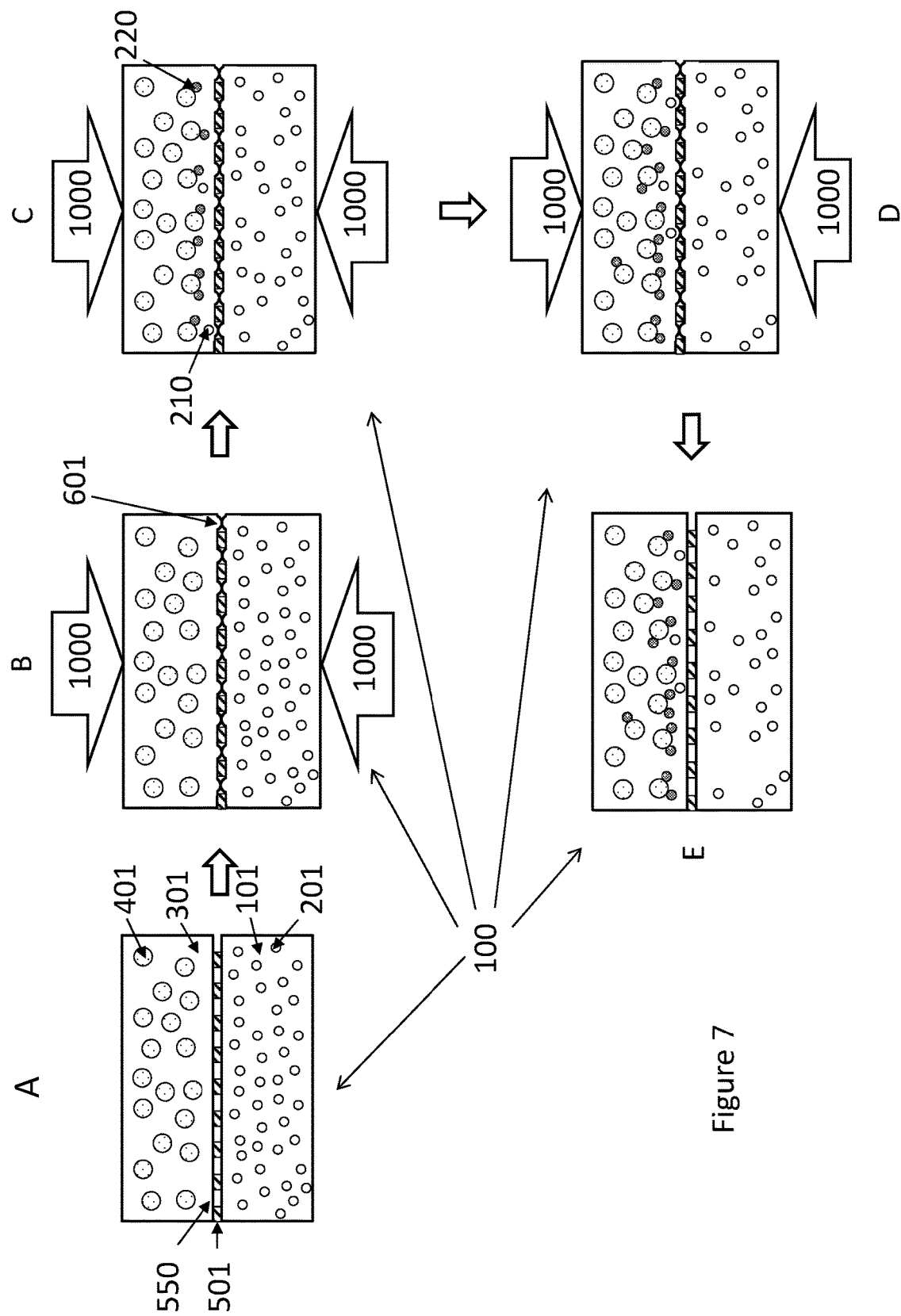
FIG. 7 is a schematic representation of an embodiment of the invention.
Figure 8:
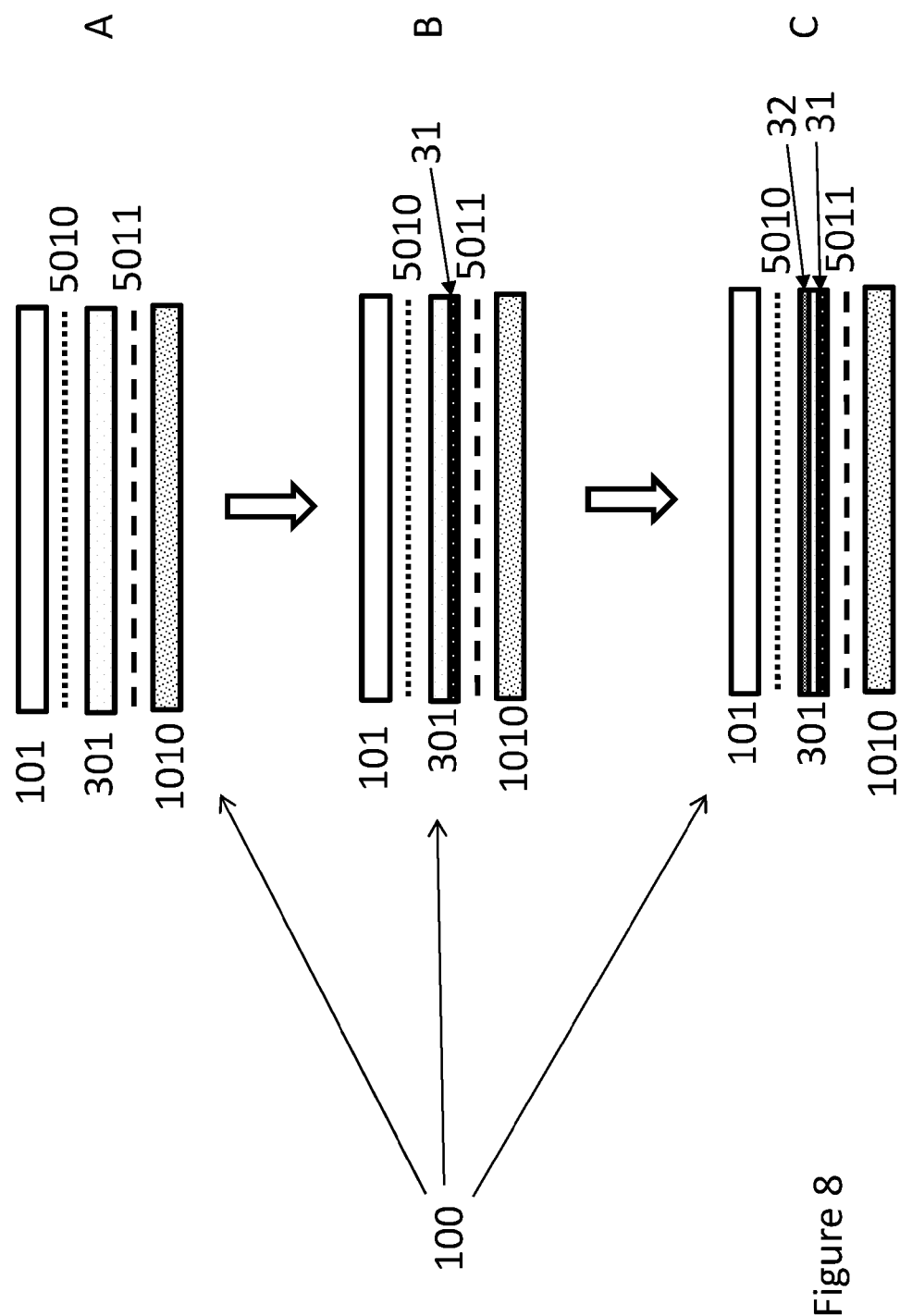
FIG. 8 is a schematic representation of an embodiment of the invention.

The device of FIG. 8 acts to respond with different colours above different pressure thresholds (refer to FIG. 7 for mechanism of colour development). Thus, in FIG. 8B, the layer (1010) contacts the layer (301) at a lower applied pressure than the layer (101) because, for example here, the layer (5011) has larger apertures than the layer (5010).

The colour (31) developed in the layer (301) results from the colour former contained within the layer (1010) at specific locations when a lower pressure threshold is exceeded. In FIG. 8C, when a second, higher pressure threshold is exceeded, the colour (31 and 32) developed in the layer (301) results from both the colour former contained within the layers (1010) and (101), resulting in a different colour than for the colour (31) alone. In this manner, the device can report different colours at two or more different pressure thresholds.

Figure 9:
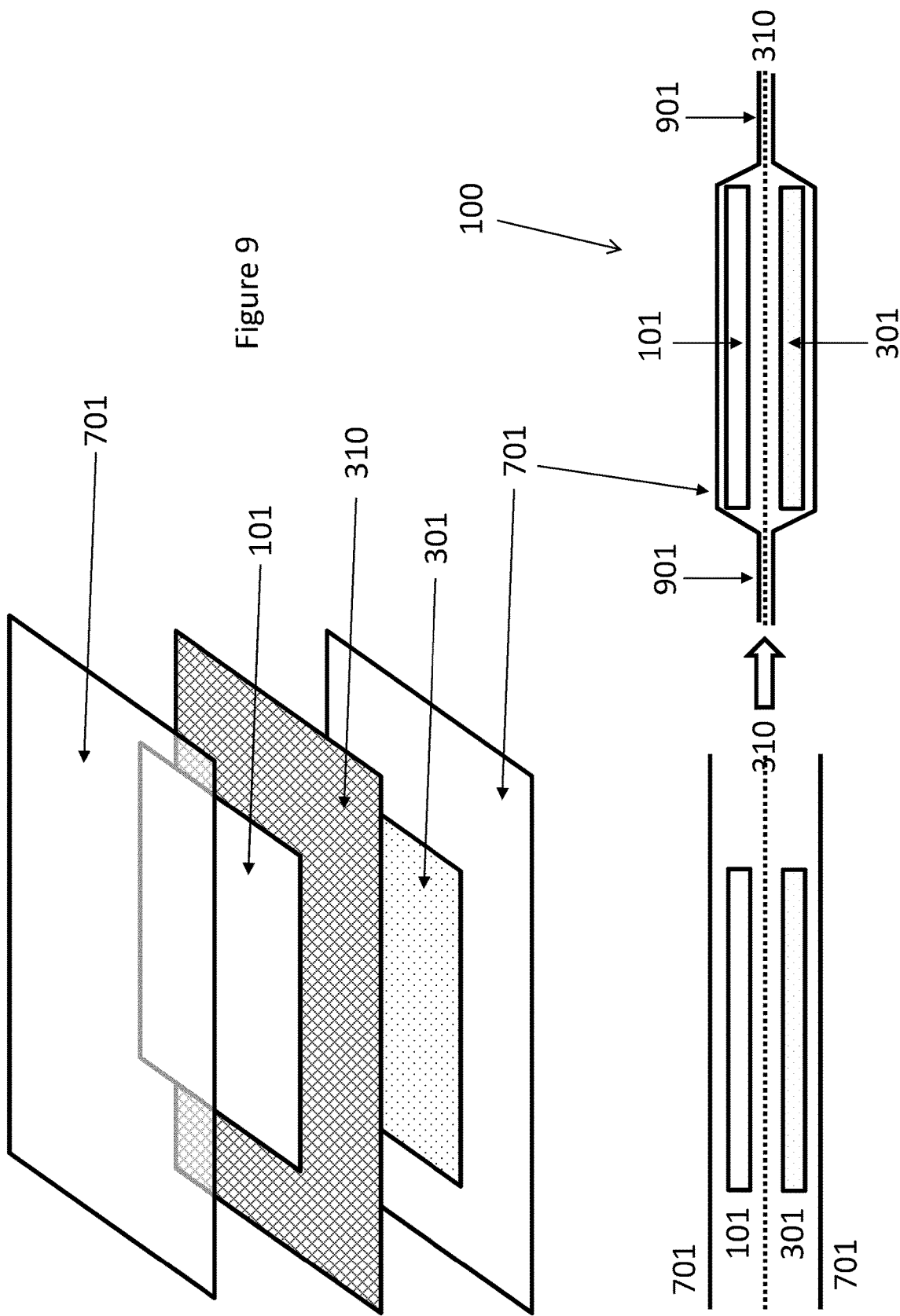
Figure 10:
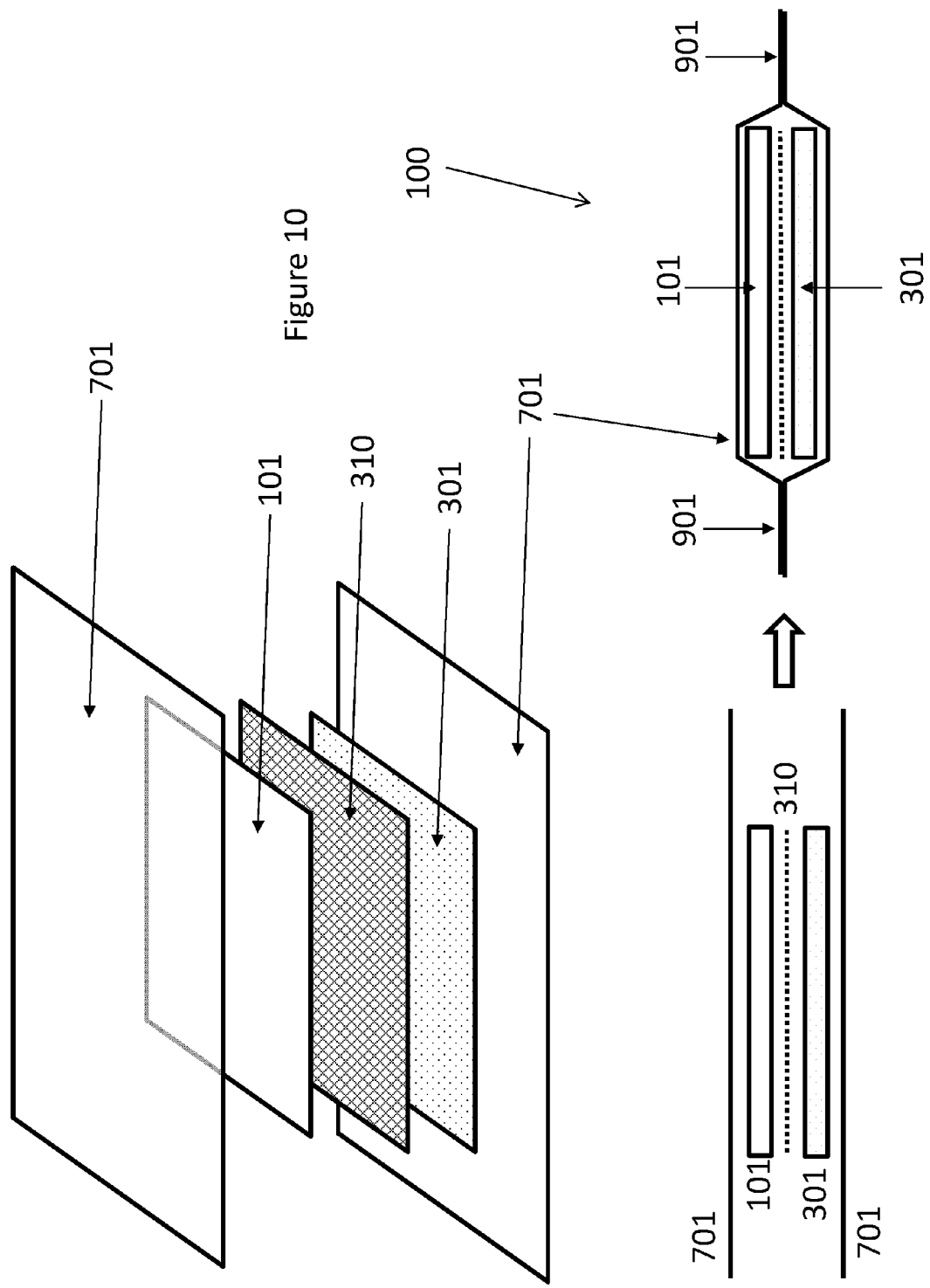
Figure 11:
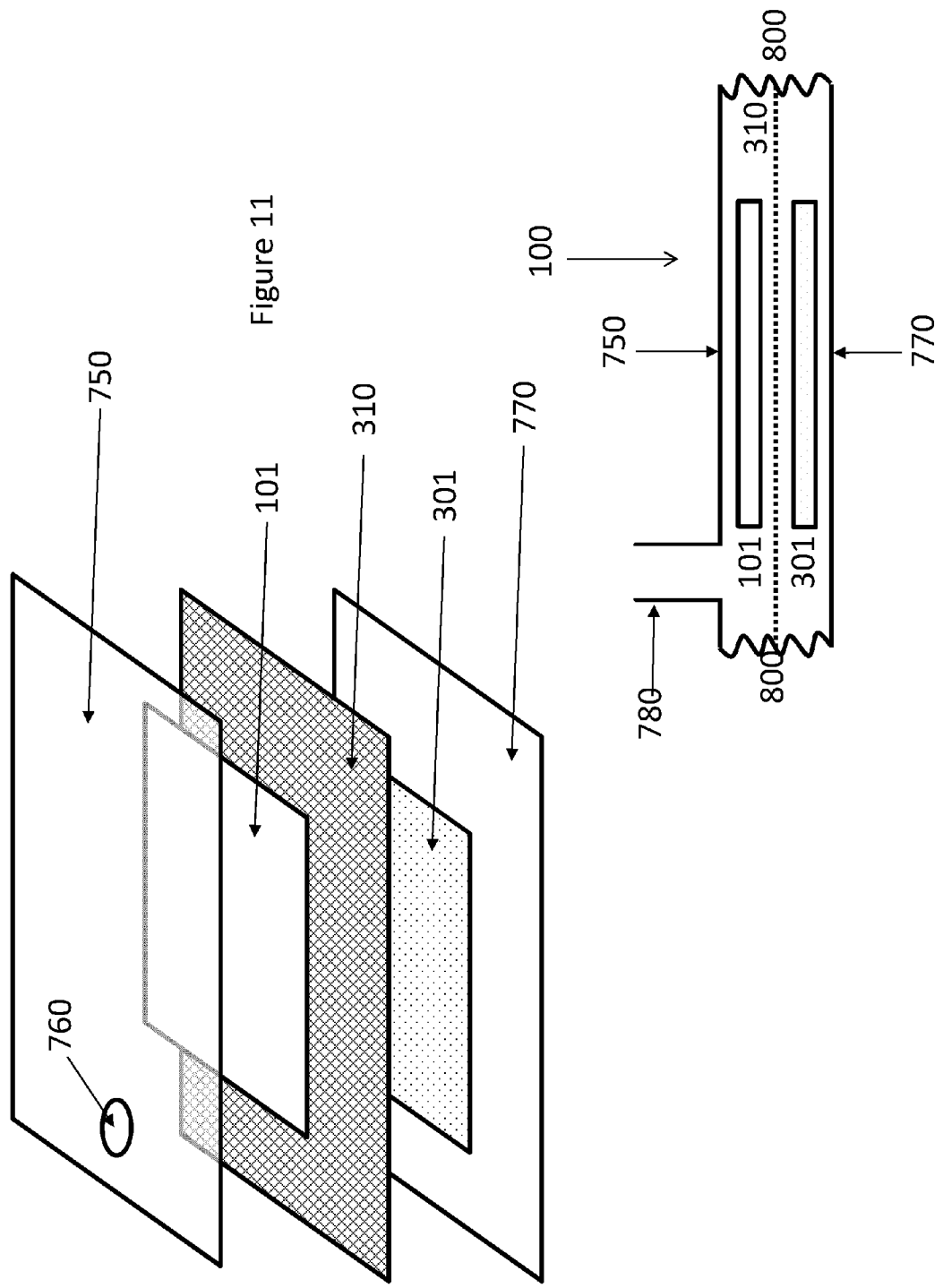
Figure 12:
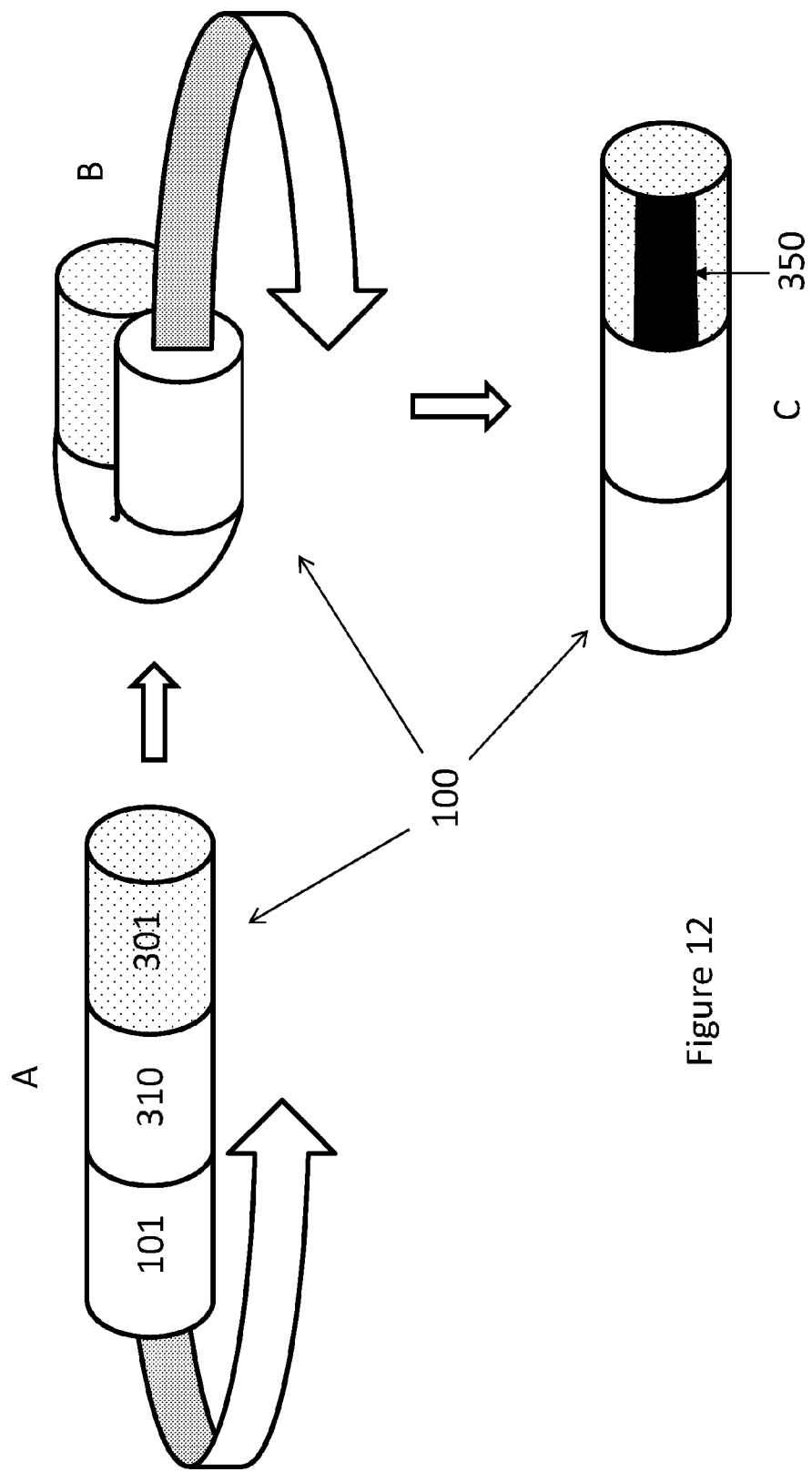
Figure 13:
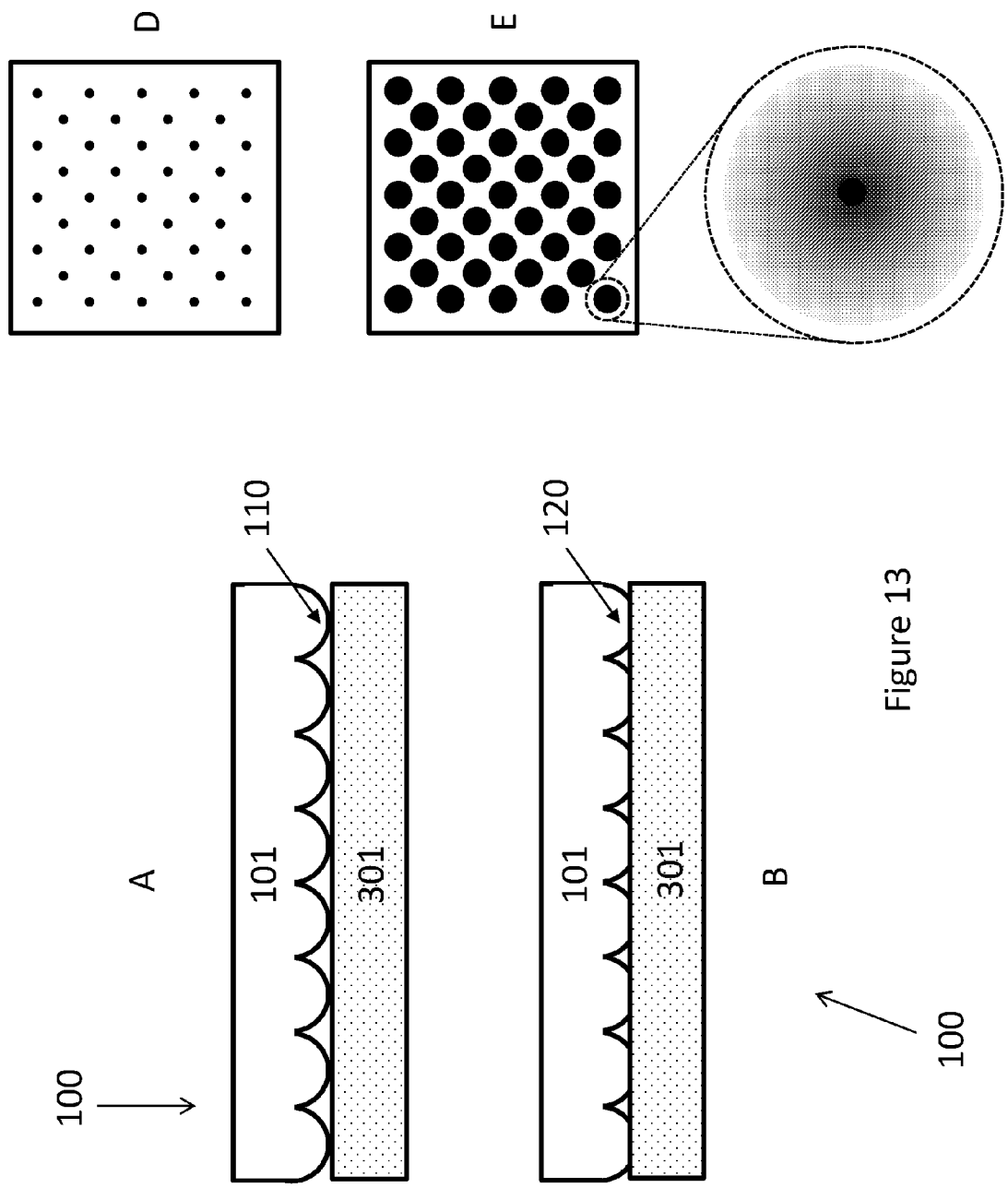
Figure 14:
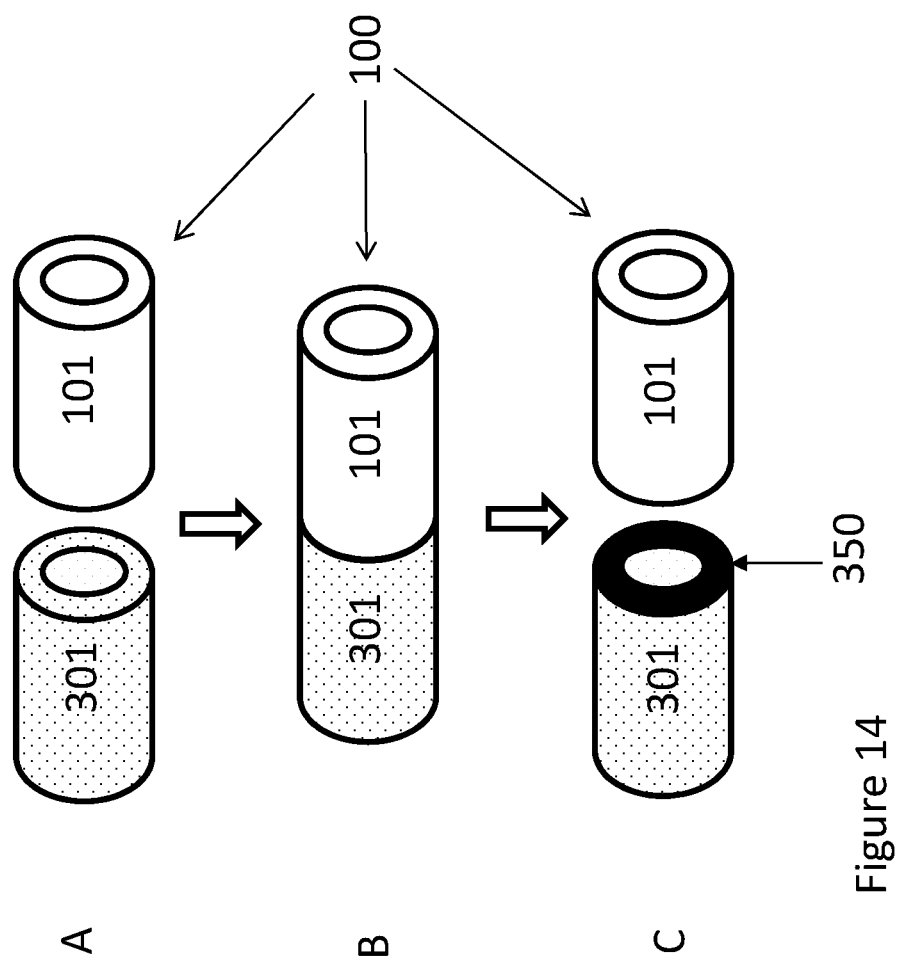
Figure 15:
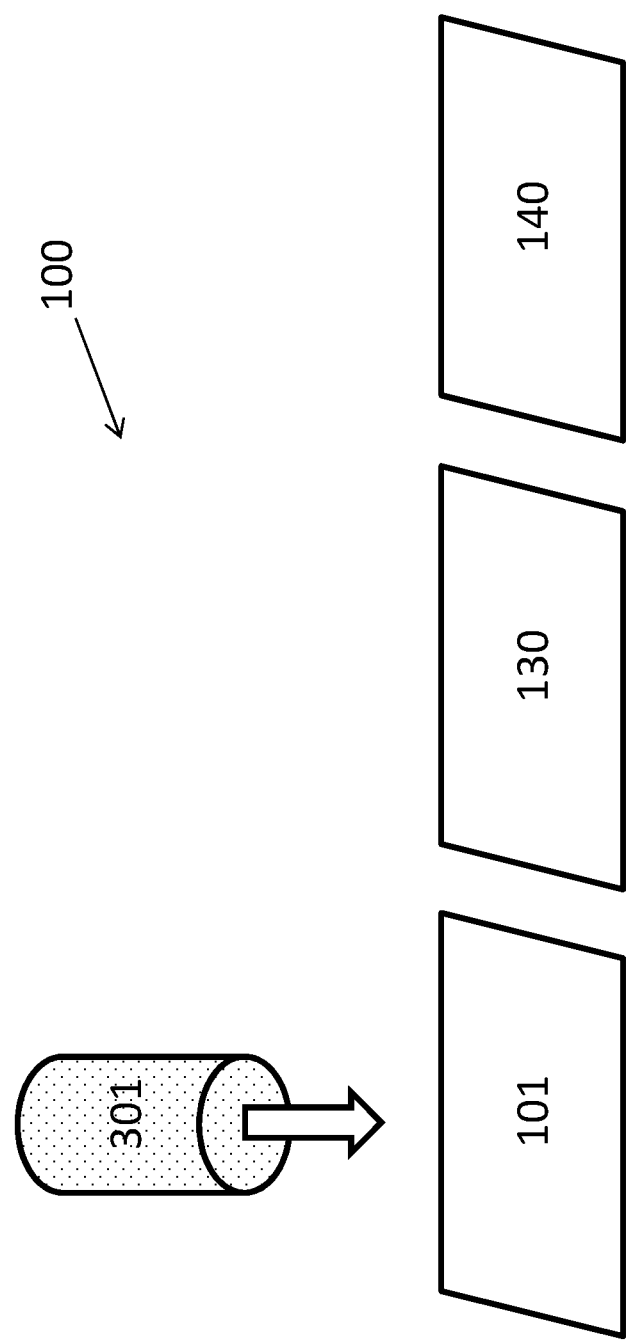
Figure 16:
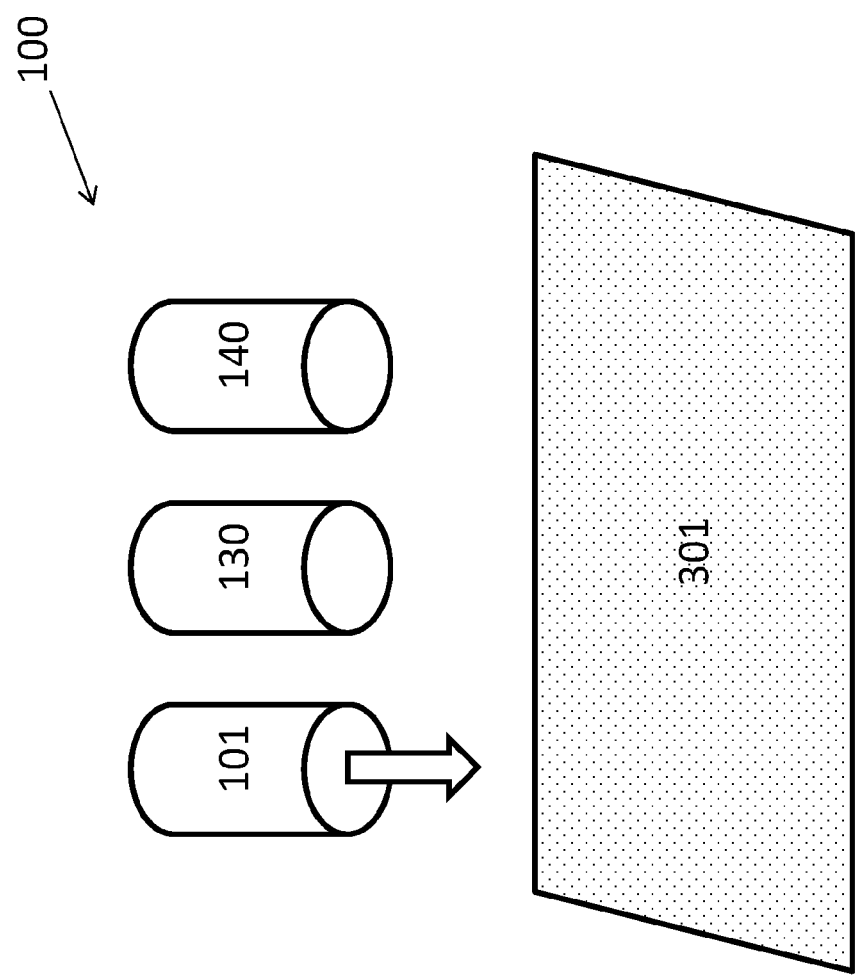
Figure 17:
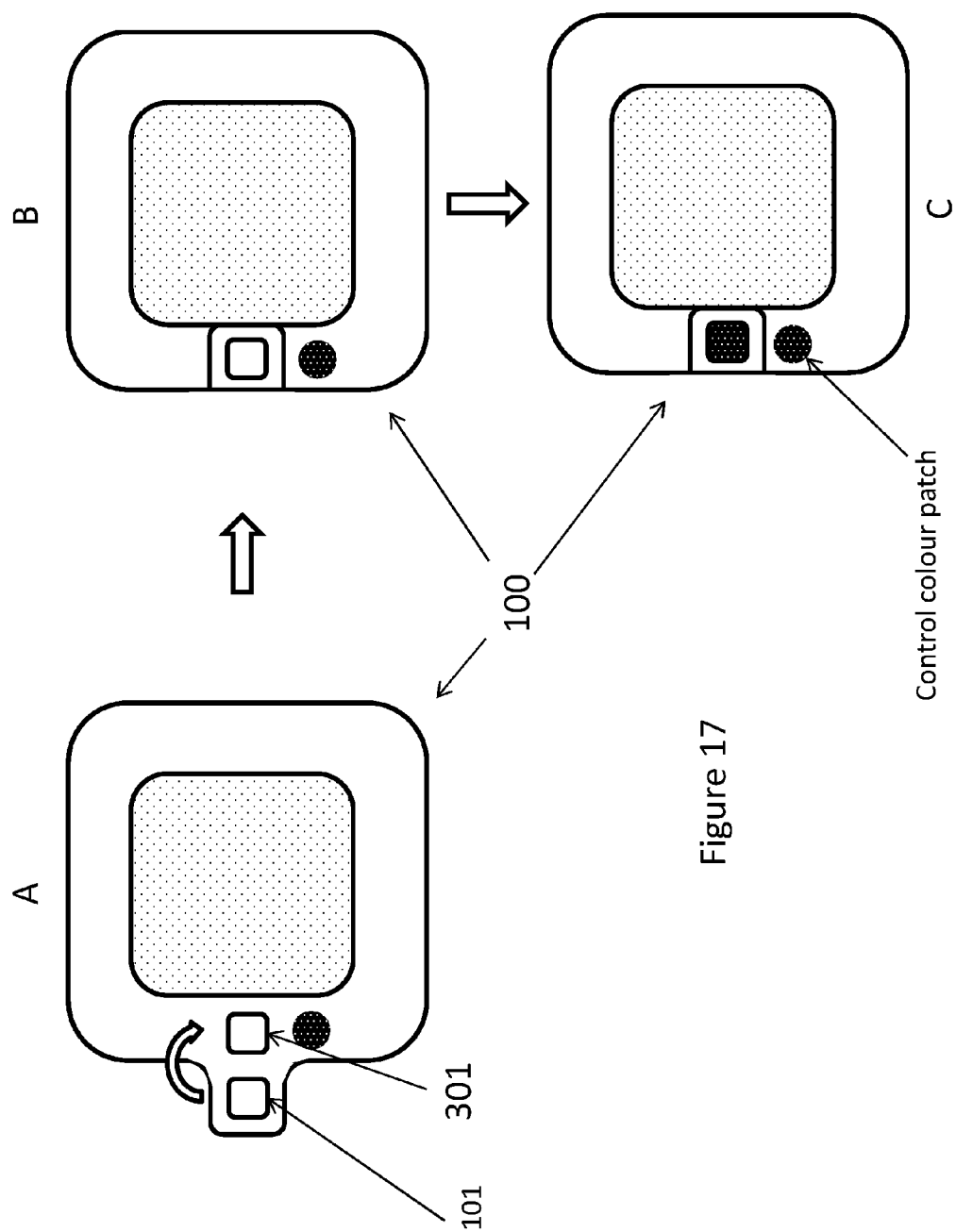

FIG. 9 illustrates a device (100) of certain embodiments of the invention for the measurement of the duration and location of an applied pressure, comprising a first element (101) in which is dispersed a colour-forming dye in its uncoloured state and a second element (301) in which is immobilised a particulate colour developer. These two elements are separated by a third element (310) which contains apertures and of an area larger and extending beyond the perimeter of the first element and second element. Two sheets of flexible transparent film (701) are positioned on the remaining faces of the first element and second element, of the same area as the third element. The third element and the film are associated at their perimeter (901) to immobilise the first element and second element in place;

FIG. 10 illustrates a similar device (100) to the device of FIG. 9, except that the third element (spacer layer) (310) is cut to the same size as the layer (101) and the layer (301);

FIG. 11 illustrates a device (100) of certain embodiments of the invention for the measurement of the duration of an applied vacuum (a reduced pressure), comprising a first element (101) in which is dispersed a colour-forming dye in its uncoloured state and a second element (301) in which is immobilised a particulate colour developer. These two elements are separated by a third element (310) which contains apertures and of an area larger and extending beyond the perimeter of the first element and second element. Two sheets of a rigid transparent material (750) and (770) are positioned on the remaining faces of the first element and second element, of the same area as the third element. The rigid transparent layer (750) has a single aperture (760) for communication with a potential source of vacuum via an adaptor (780). The layers (310), (750) and (770) are associated at their perimeter by a flexible seal (800). When a vacuum is applied via the adaptor (780), the rigid layers (750) and (770) are forced together by atmospheric pressure and, above a certain vacuum threshold, cause the first and second elements to contact one another via the apertured layer (310);

FIG. 12A illustrates a device (100) of certain embodiments of the invention for the measurement of the duration of a specific contact geometry comprising a first element (101) in which is dispersed a colour-forming dye in its uncoloured state and a second element (301) in which is immobilised a particulate colour developer. These two elements are separated by a flexible third element (310), impermeable to the colour-former. When this device is folded in half (FIG. 12B), the elements (101) and (301) come into contact, the extent of which is determined by the magnitude of the applied force. Colour develops in the second element (301) for periods when the first element and the second element are in contact and the extent of colour development (350) can be assessed during or following use when the device is in its unfolded geometry (FIG. 12C);

FIG. 13A illustrates a device (100) of certain embodiments of the invention that can measure the duration and magnitude of an applied force, but in the absence of a third element, comprising a first element (101) with surface protrusions (110) in which is dispersed a colour-forming dye in its uncoloured state and a second element (301) in which is immobilised a particulate colour developer. These two elements are in contact via the tips of the surface protrusions (110) and aptly the contact area is less than 10% of the face area of the second element. In the absence of an applied force, colour is developed in the second element 301 at these contact points only, as shown in FIG. 13D. Meanwhile, if the device is subject to a compressive force perpendicular to its largest face, the surface protrusions become compressed (120) against the second element (301), as shown in FIG. 13B, and this leads to colour development across a greater surface area of each protrusion, as shown in FIG. 13E. Thus the device develops colour at each protrusion at an intensity proportional to the duration of the applied pressure and a radial distance proportional to the magnitude of the applied force (zero at the centre, maximum threshold at the perimeter), as also shown in FIG. 13E. The device can be calibrated for different force ranges by choosing the hardness of the solid elastomeric materials from which the first and second elements are constructed;

FIG. 14 illustrates a device (100) of certain embodiments of the invention that can measure the duration of contact between a pair of device components, here two sections of tubing. FIG. 14A illustrates a first element (101) in which is dispersed a colour-forming dye in its uncoloured state and a second element (301) in which is immobilised a particulate colour developer. These two elements are not in contact prior to use. When in use, the first element (101) and the second element (301) come into contact (FIG. 14B), enabling colour development to occur in the second element (301). When the two elements are separated during or at the end of use, the duration of contact can be determined by assessing the extent of colour development (350) in the second element (301) see FIG. 14C. This embodiment has utility to indicate the prior use of a device, particularly for devices intended for single-use;

FIG. 15 illustrates a device (100) of certain embodiments of the invention that tracks the residency time of one or more objects stationed in one or more locations. A device comprising an element (301) in which is immobilised a particulate colour-developer can, during its use, be positioned in a number of locations (or geometries). Each location (or geometry) has an element (101) in which is dispersed a colour-forming dye in its uncoloured state. In FIG. 15, each location has a different colour-forming dye in its uncoloured state: (101), (130) and (140). When the device comprising the element (301) is in contact with a given location, the colour-forming dye (101), (130) or (140) develops a location-specific colour in (301). During or at the end of use, the intensity of each colour developed in (301) can be separately read using an appropriate spectrometer (or qualitatively, by eye), thus the dwell duration at each location (or geometry) during use can be determined from the intensity of each developed colour;

FIG. 16 illustrates a device (100) of certain embodiments of the invention that track the residency time and location of one or more objects stationed in one or more locations. Each location comprising an element (301) in which is immobilised a particulate colour-developer. Each object (or several discrete locations on a single object) has an element (101) in which is dispersed a colour-forming dye in its uncoloured state. In FIG. 16, each object has a different colour-forming dye in its uncoloured state: (101), (130) and (140). When the objects comprising (101), (130) or (140) are in contact with a given location (301), the colour-forming dye (101), (130) or (140) develops an object-specific colour in the location 301. During or at the end of use, the intensity and location of each colour developed in the location 301 can be separately read using an appropriate spectrometer (or qualitatively, by eye), thus the dwell duration of each object at each location (or geometry) during use can be determined from the intensity of each developed colour;

FIG. 17 illustrates a device (100) of an embodiment of the invention which is a use duration indicator for a topical device e.g. a drug delivery patch or a wound dressing. The two small squares in FIG. 17A are a first element comprising the colour forming material (101) and a second element comprising a colour developing material (301) and these elements are brought together (arrow in FIG. 17A) at the commencement of use, as shown in FIG. 17B. This can happen automatically (due to design) or be performed by the user.

Figure 18:
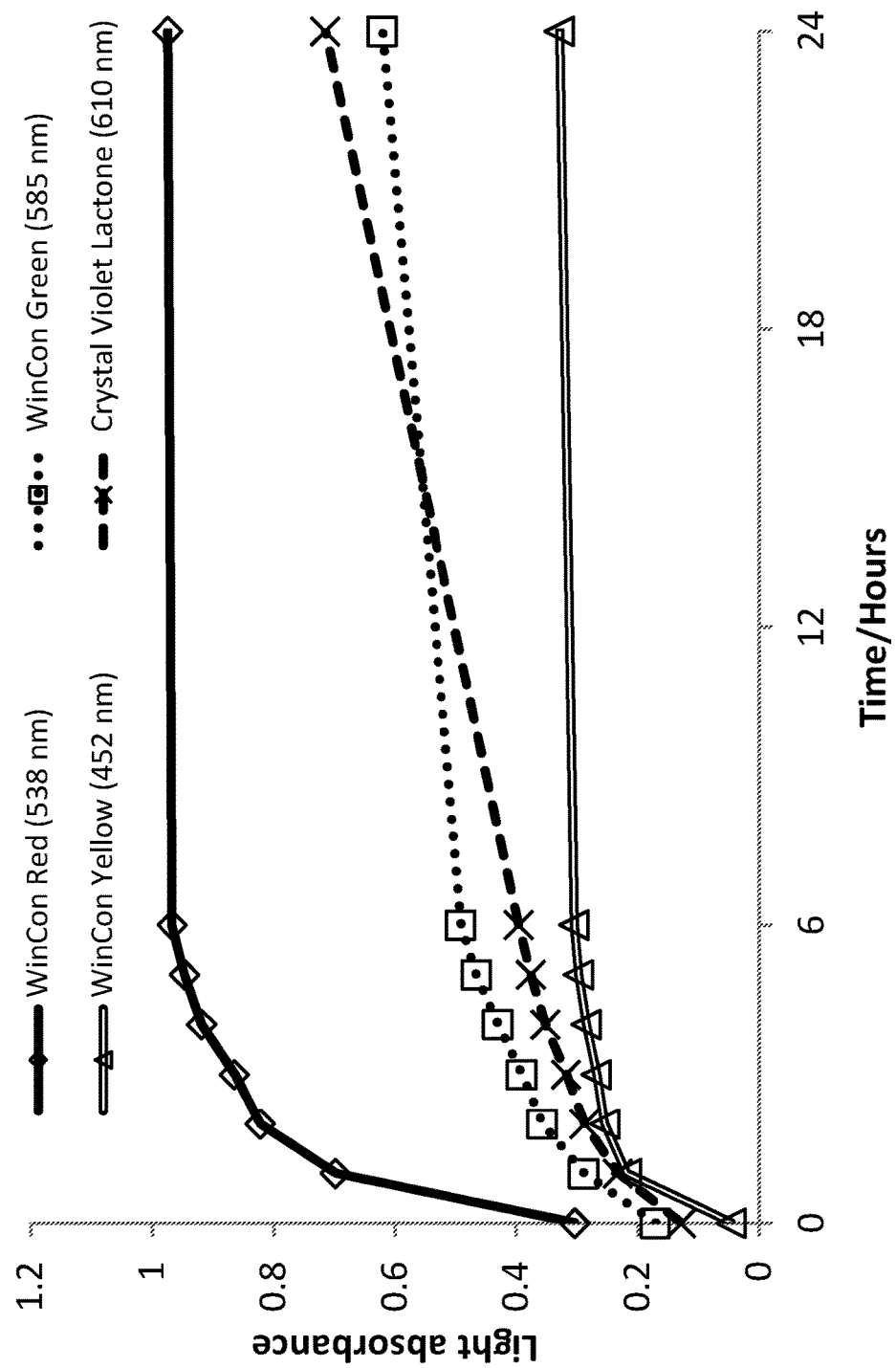
Figure 19:
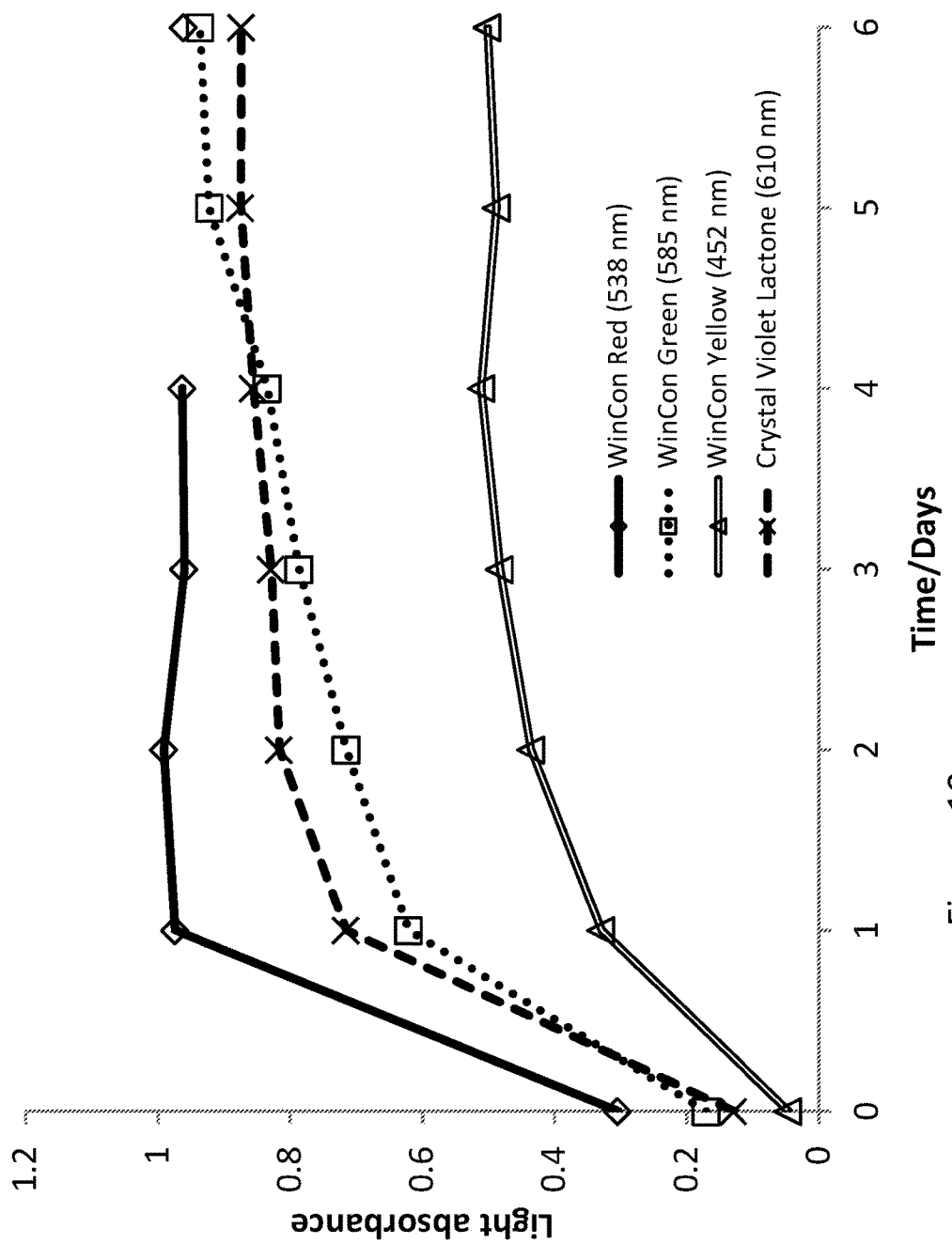
Figure 20:
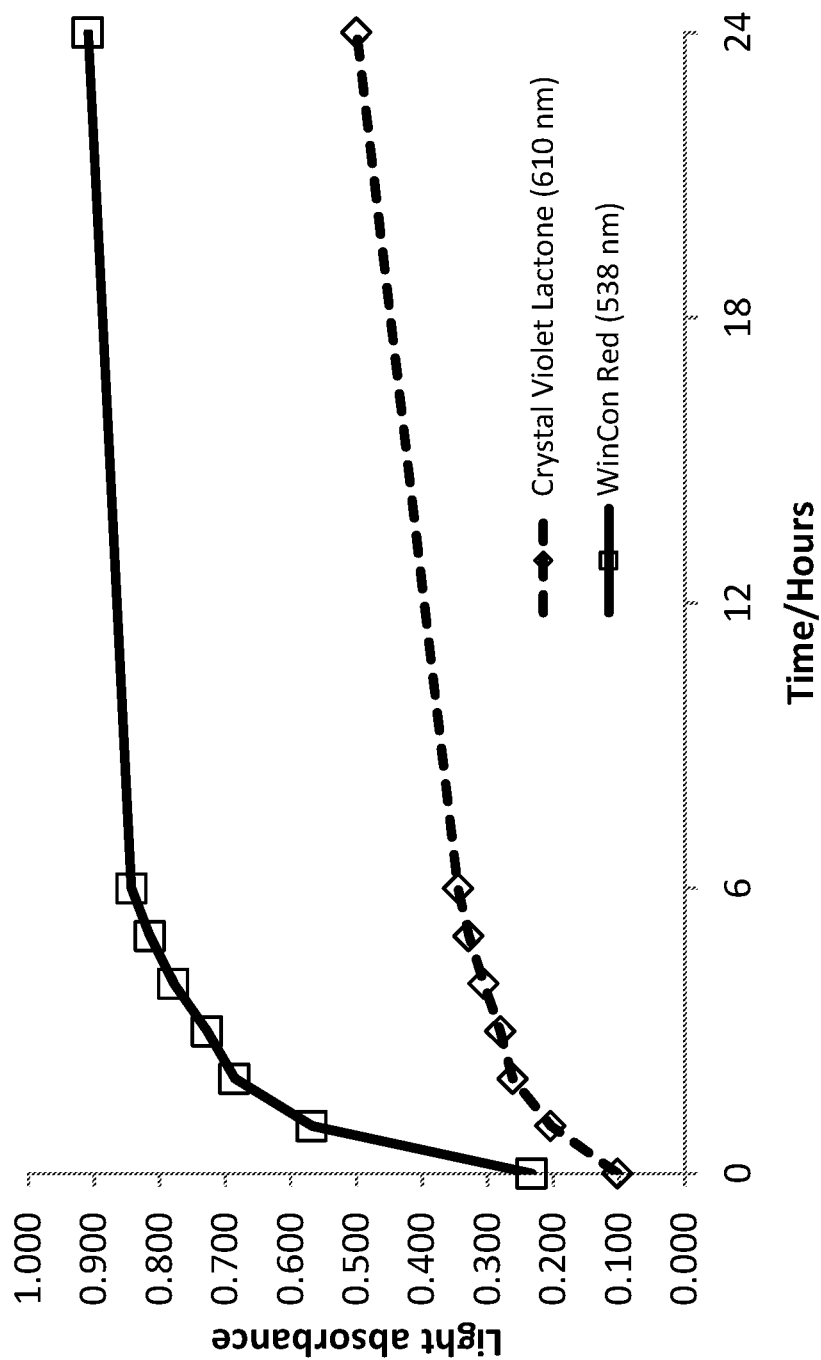
Figure 21:
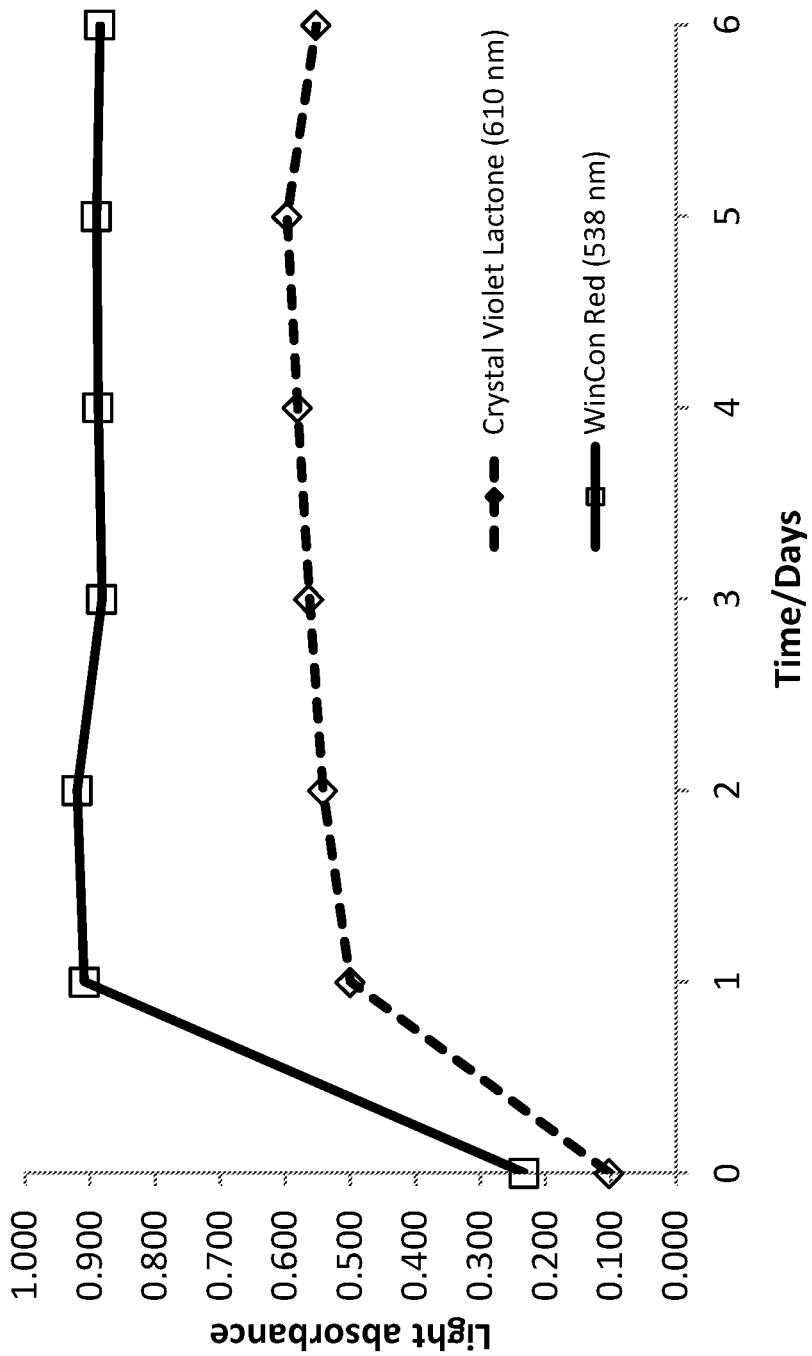
Figure 22:
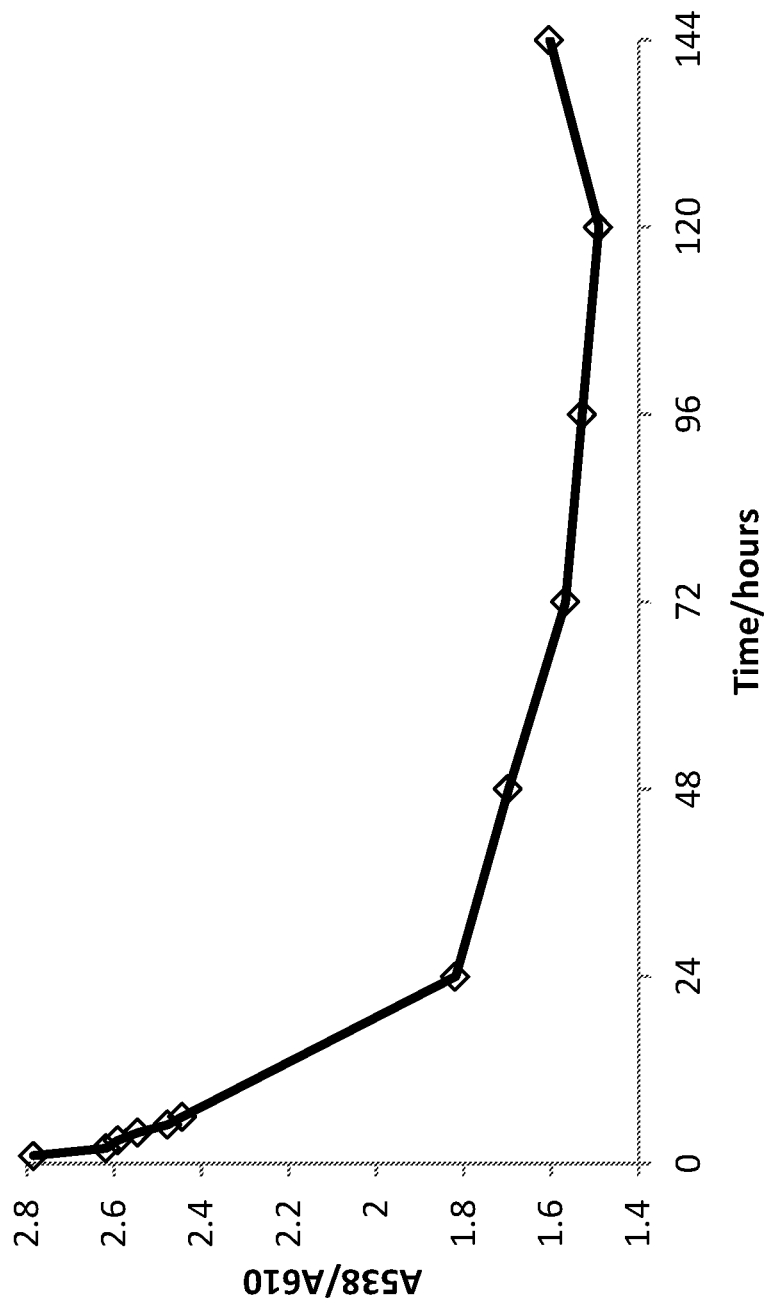
Figure 23:
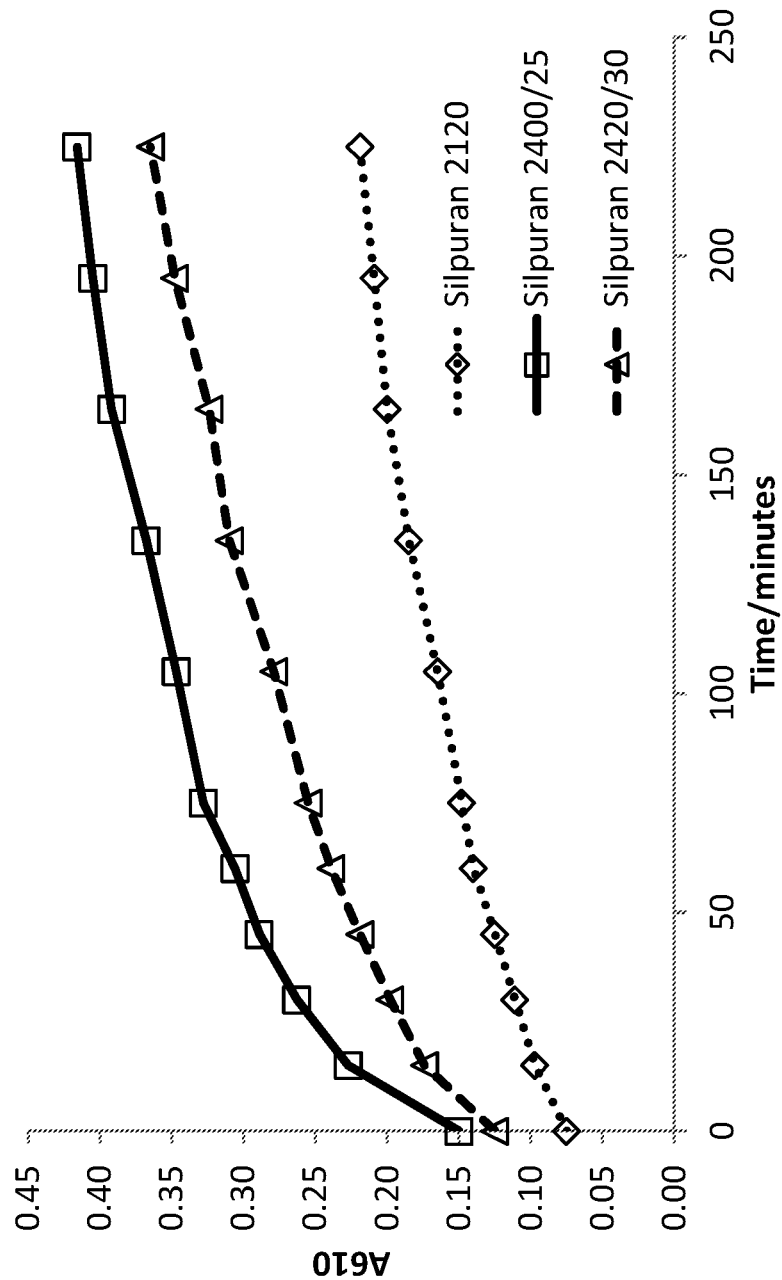
Figure 24:
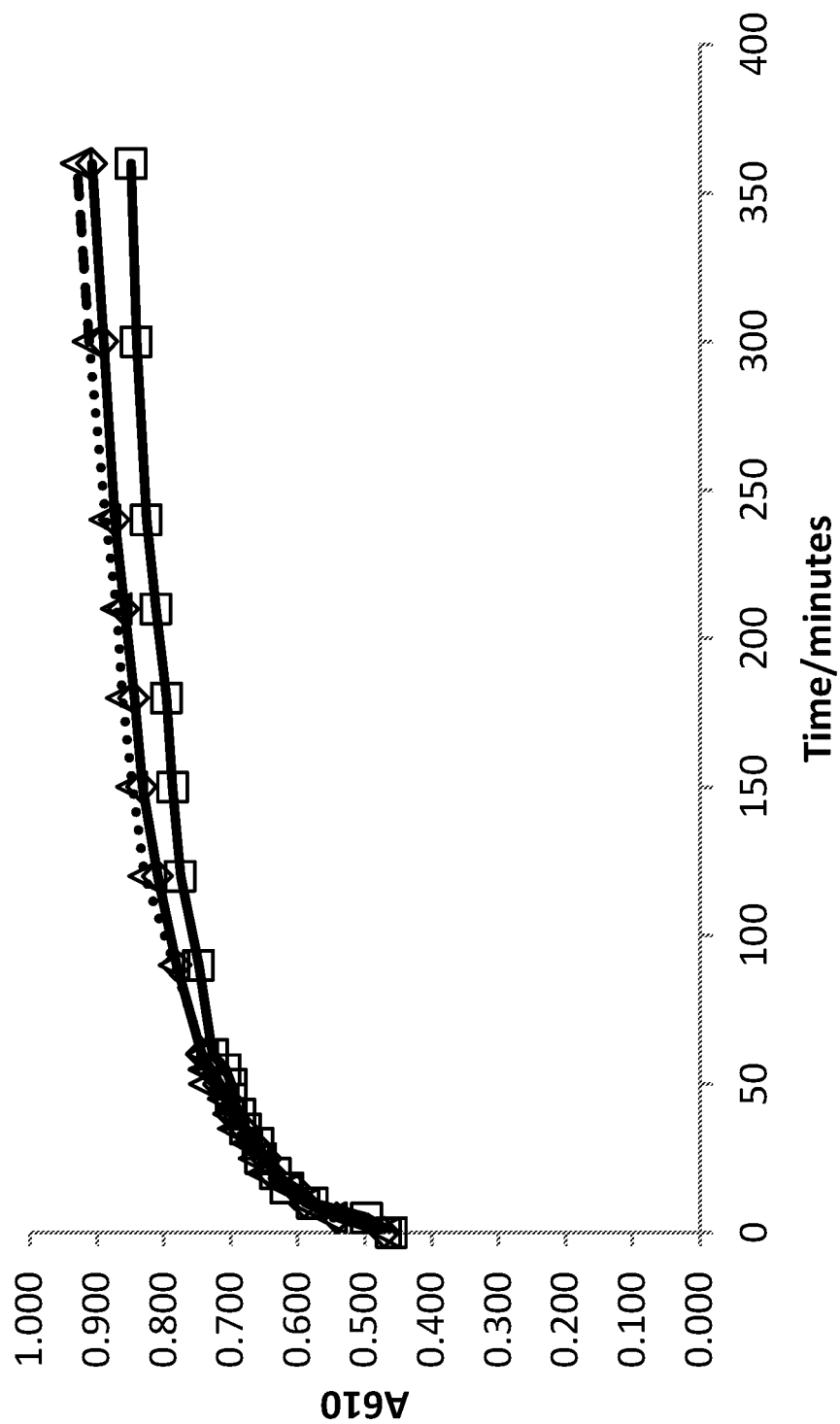
Figure 25:
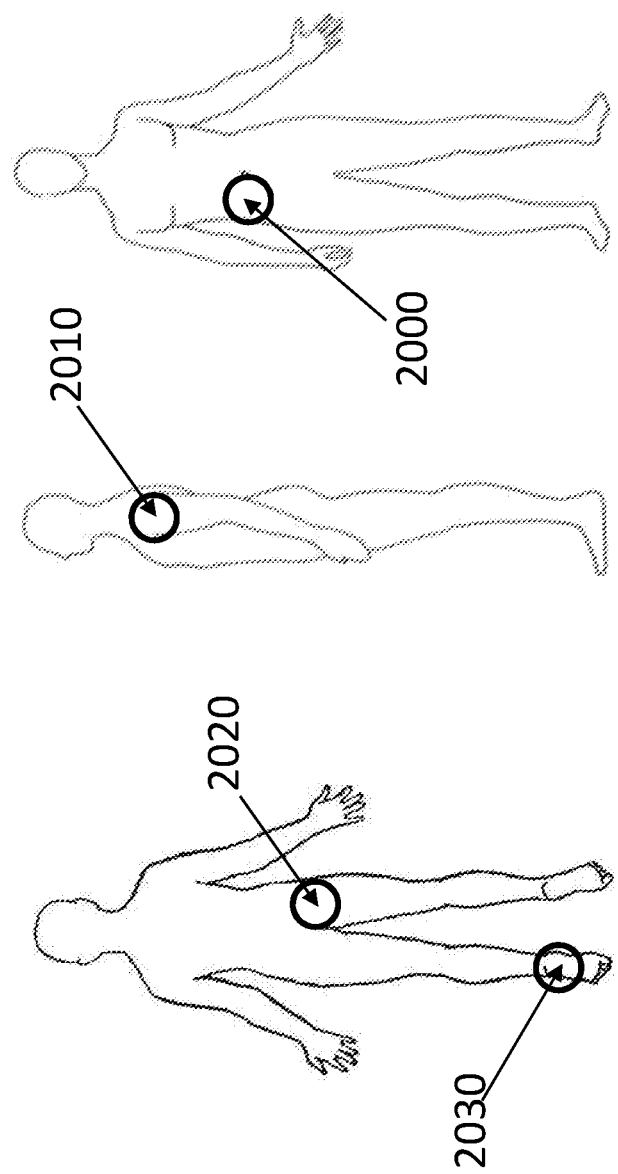
Figure 26:
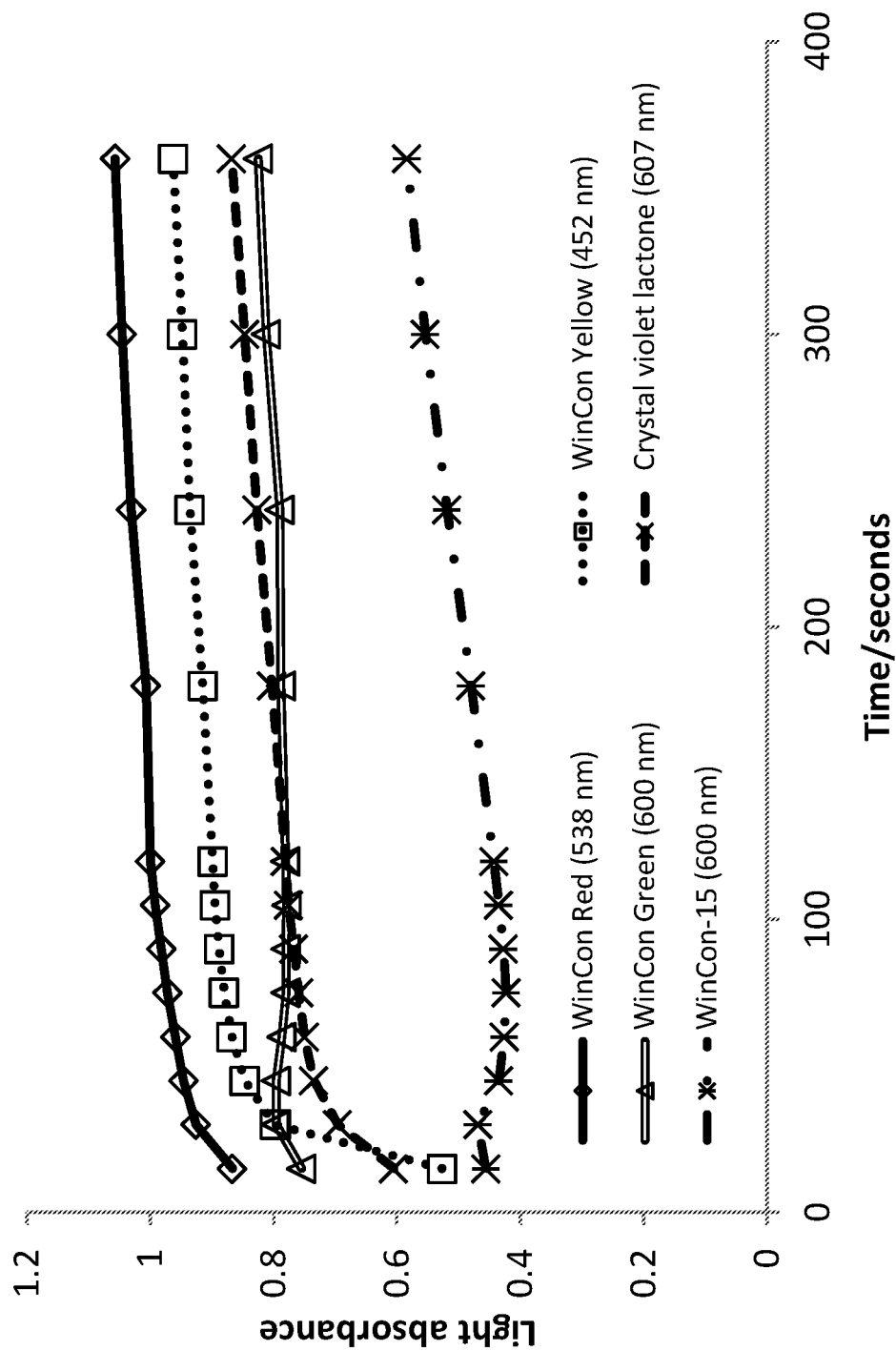

During use, the developed colour is compared to a control colour patch (the circular dot) to determine when the therapy has been completed, as shown in FIG. 17C;

FIG. 18 is a graph illustrating the colour intensity results of Example 7, i.e. the colour intensity produced by devices of Examples 1, 2, 4 and 5 over several hours;

FIG. 19 is a graph illustrating the colour intensity results of Example 7, i.e. the colour intensity produced by devices of Examples 1, 2, 4 and 5 over several days;

FIG. 20 is a graph showing the results of Example 8 over several hours;

FIG. 21 is a graph showing the results of Example 8 over several days;

FIG. 22 is a graph illustrating the results of Example 8;

FIG. 23 is a graph illustrating the results of Example 9;

FIG. 24 is a graph illustrating the results of Example 10;

FIG. 25 is a graphic representation of placement of a device as described in Examples 13 and 15;

FIG. 26 is a graph illustrating the results of Example 21; and

Figure 27:
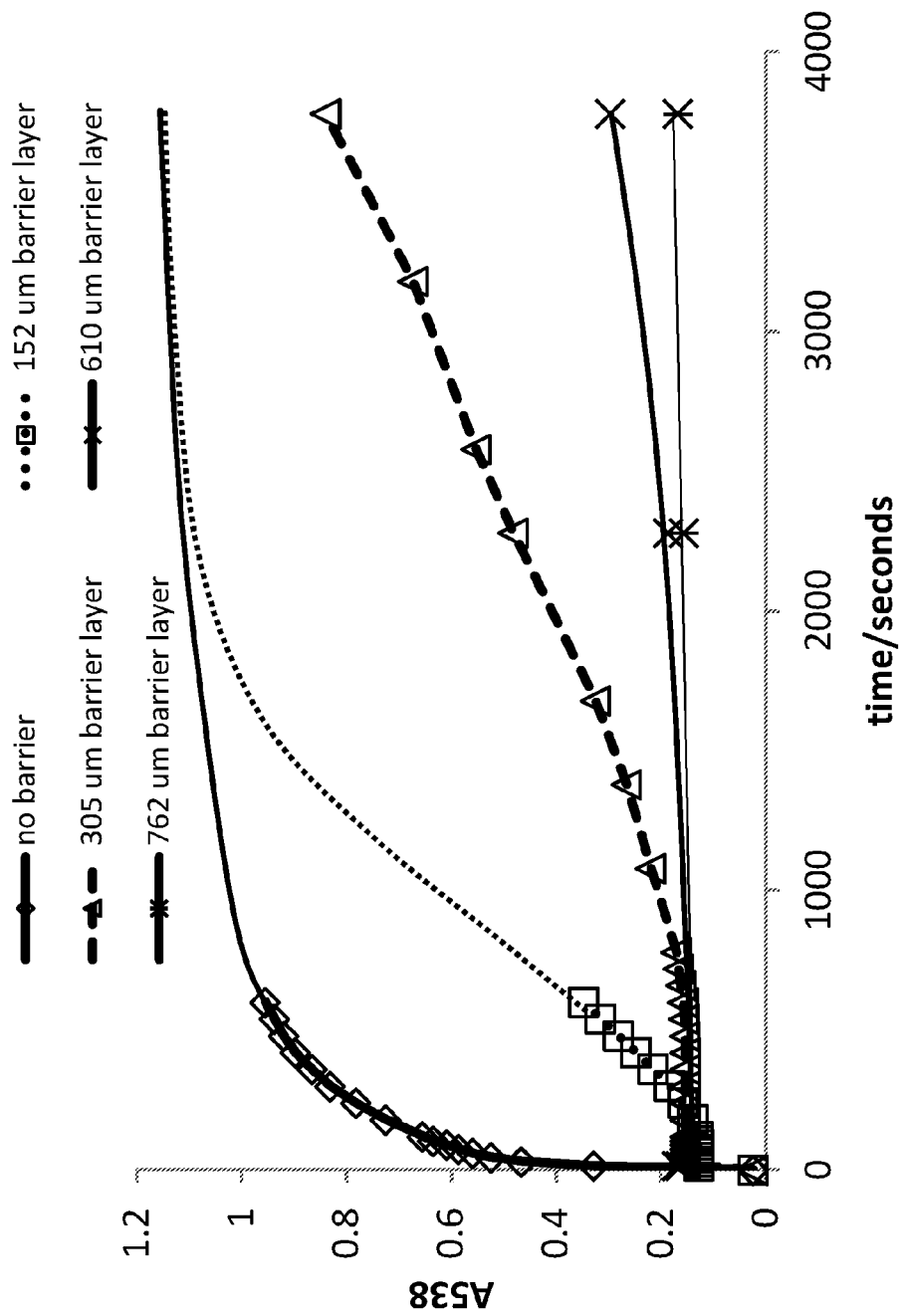

FIG. 27 is a graph illustrating the results of Example 22.

Figure 28:
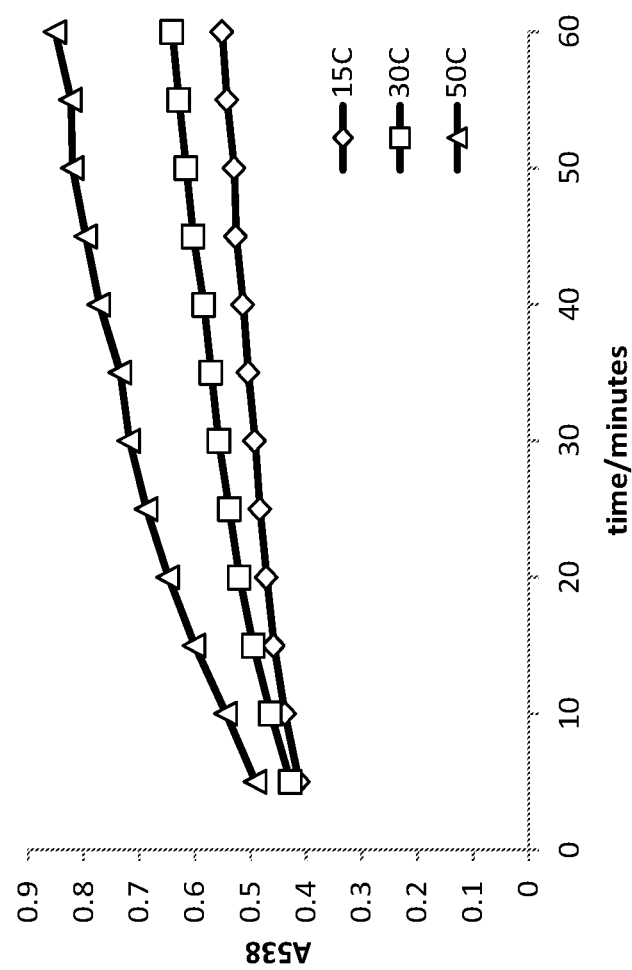

FIG. 28 is a graph illustrating the results of Example 27.

Figure 29:
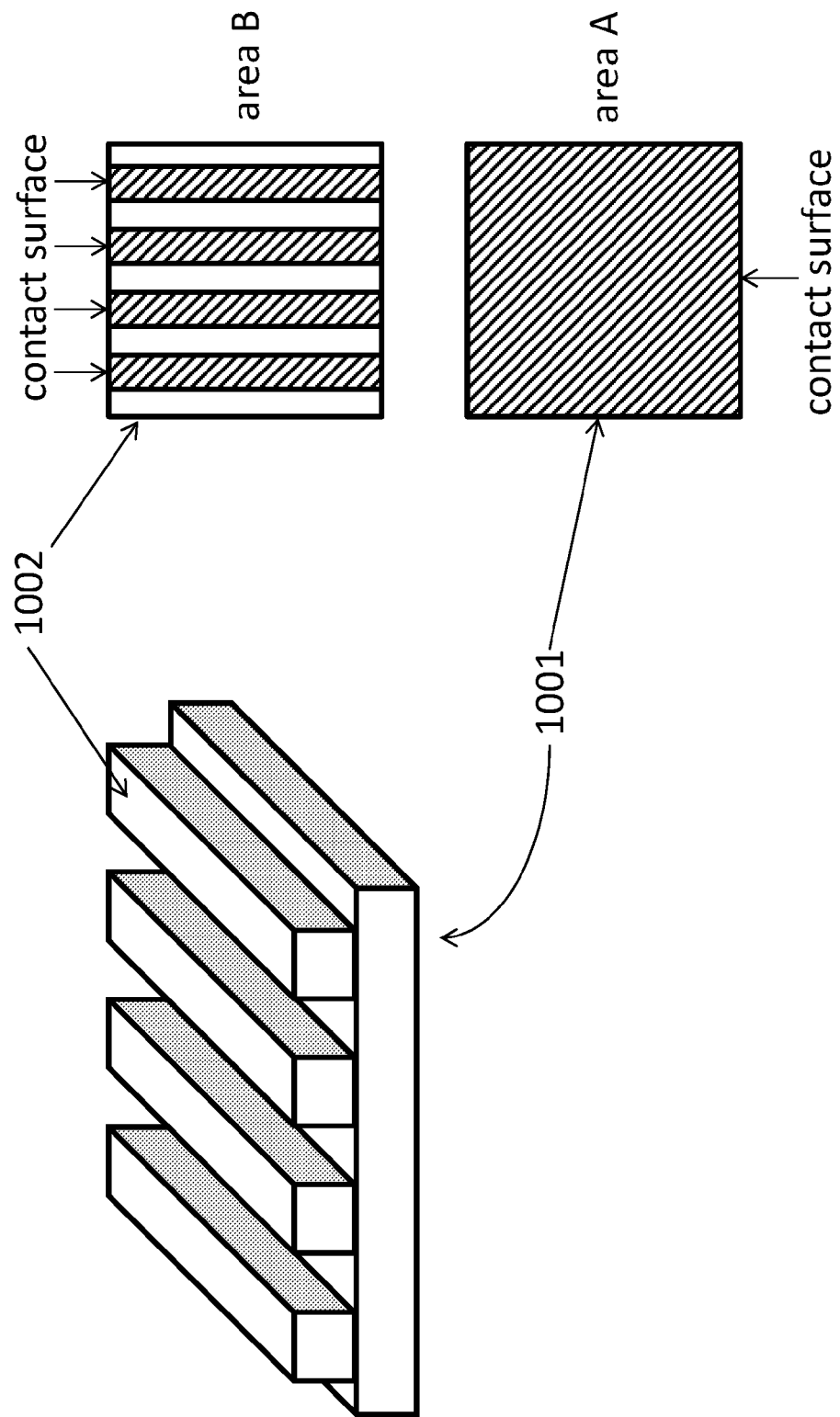

FIG. 29 illustrates a device of certain embodiments of the present invention which comprises a first and/or a second element that is textured on one or both faces for the concentration of applied pressure. The first and/or second element comprises a first flat (or differently textured) face (1001) of a contact surface area 'A' and a second textured face (1002) of a contact surface area 'B'. As shown in FIG. 29, the, surface area 'A' is approximately double that of 'B'. If a pressure is applied to the face (1001) of this element it will be transmitted to associated underlying elements via the face (1002). For the full area of the element, the total pressure transmitted will be the same as the pressure applied but the total pressure applied by the surface protrusions 1002 will be approximately double that being applied across the face (1001). Utilising this principle, the minimum threshold of pressure detection for devices and apparatus of embodiments of the present invention can be raised by a factor of (surface area A/surface area B). Aptly, contact area B is about 10% or greater than the area of contact area A. Aptly, the pressure concentration is up to about 10-fold.

Figure 30:
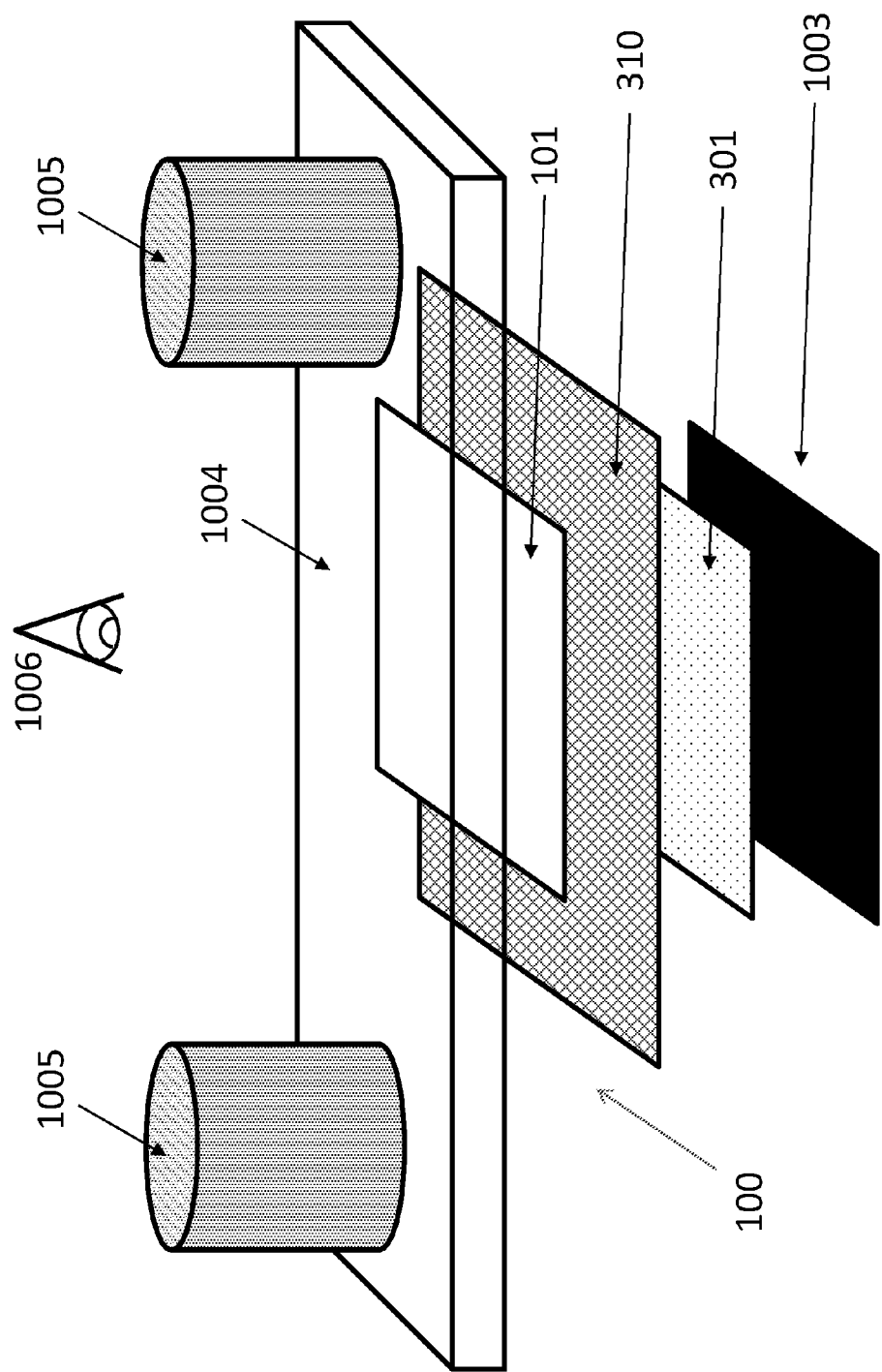

FIG. 30 illustrates a device (100) of certain embodiments of the invention for the measurement of the duration and location of an applied pressure. Its use is described in Example 31. The device comprises a first element (101) in which is dispersed a colour-forming dye in its uncoloured state and a second element (301) in which is immobilised a particulate colour developer. These two elements are separated by a third element (310) which contains apertures and of an area larger and extending beyond the perimeter of the first element and second element;

The associated layers are positioned upon a flat, opaque, strongly-coloured surface (1003) of the same or larger perimeter dimensions than the second element (301). The black back of a mirrored glass tile is an example of a suitable surface.

Upon the associated layers is positioned a layer of inflexible transparent material (1004). A sheet of toughened glass of thickness greater than 5 mm is suitable. The material (1004) has perimeter dimensions larger than the second element (301) and extending significantly in one axis to enable the positioning of equal weights (1005) at its ends without obstructing view of the associated device layers.

In use, weights (1005) are added incrementally until contact occurs between the layers (101) and (301) via the apertured layer (310). Contact is immediately visible to the observer (1006) as a strong colouration of the associated layers at the contact locations. The colouration is due to increased light transmission via the contact surface, transmitting the colour of the strongly-coloured surface (1003).

Figure 31:
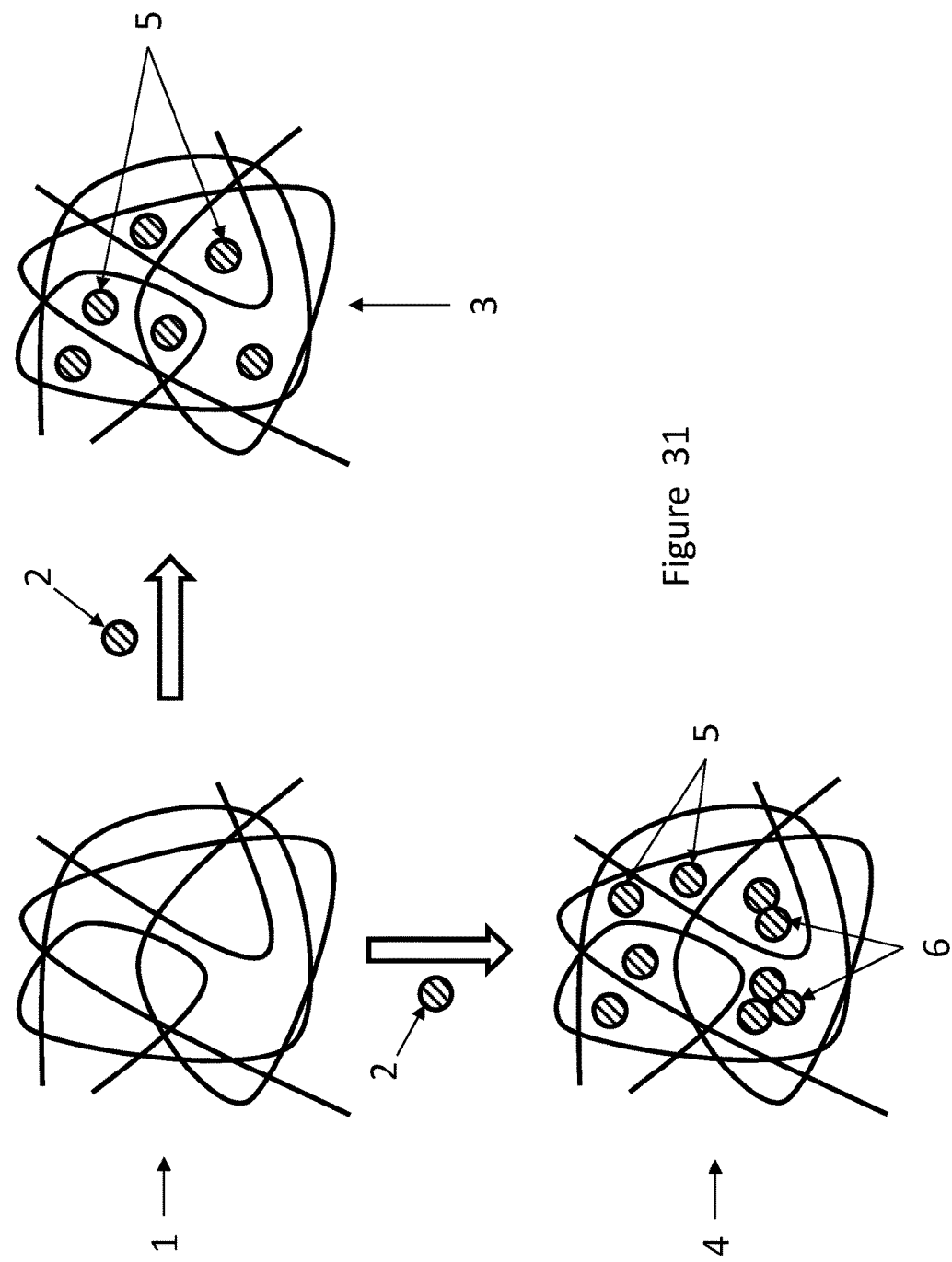
Figure 32:
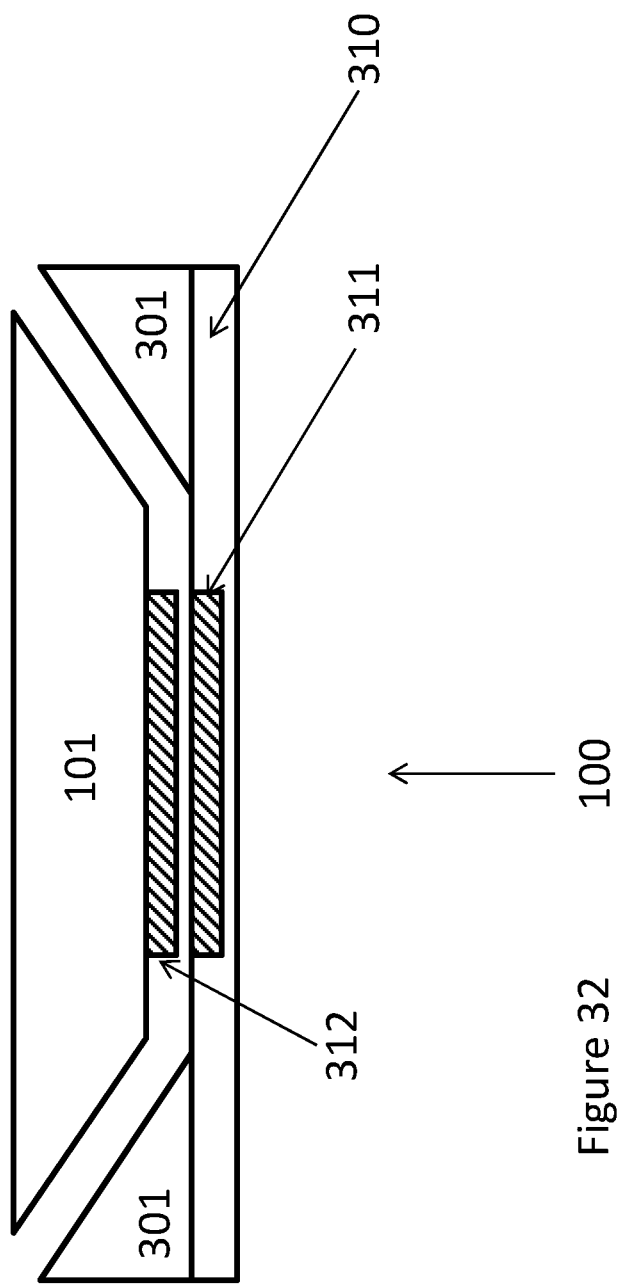
Figure 33:
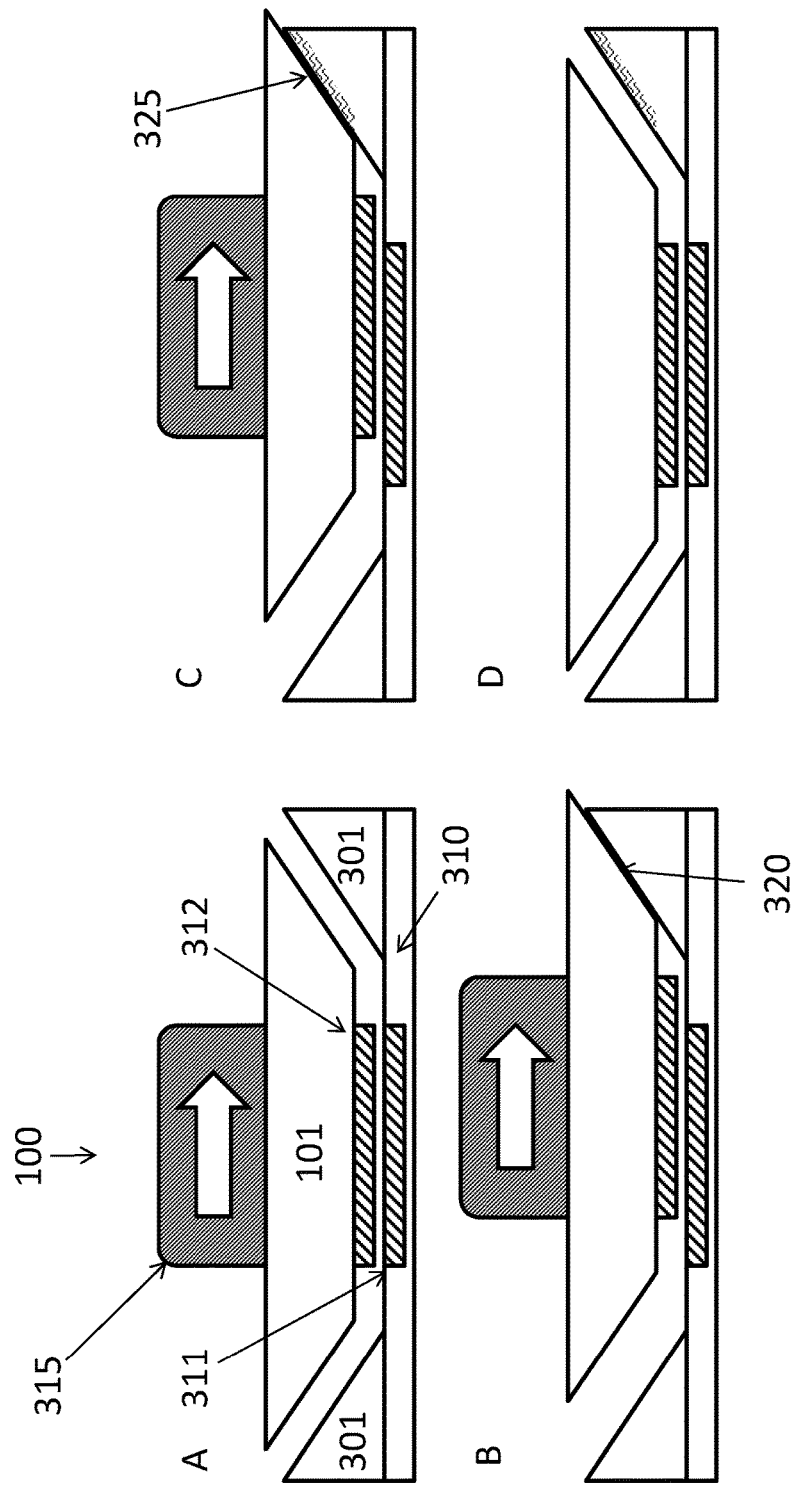
Figure 34:
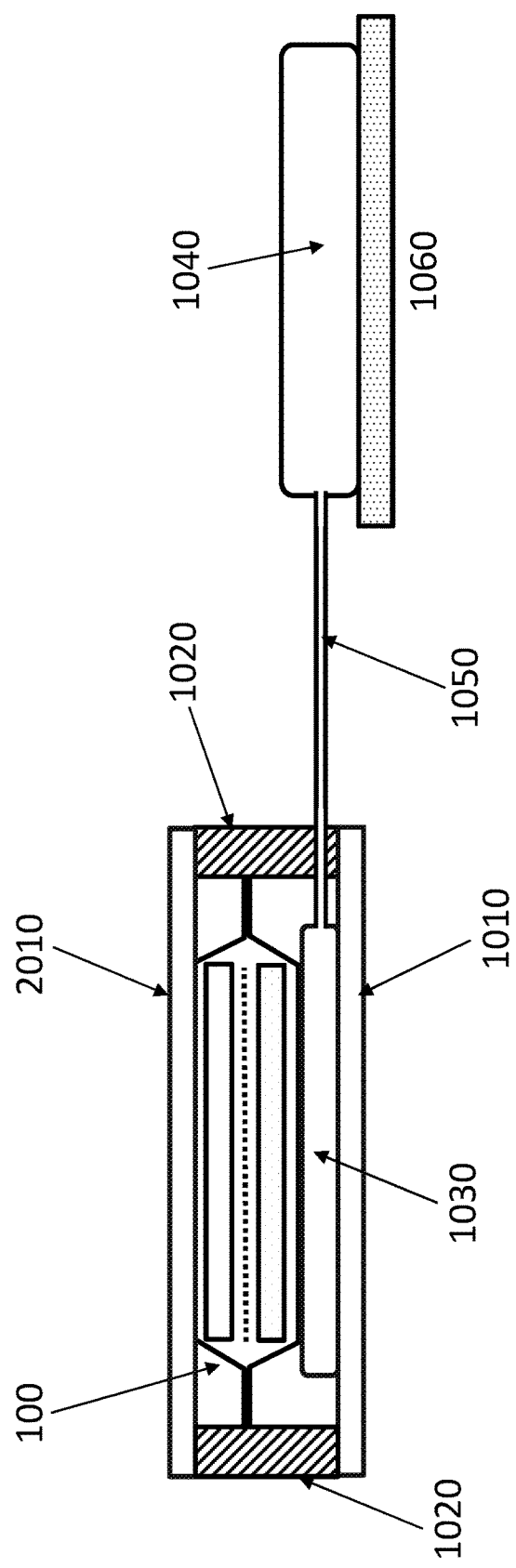

In this way, the pressure threshold of a given device arrangement can be determined in an experimentally convenient and rapid manner. This arrangement also allows pressure to be applied to a test device in a homogeneous manner by fine adjustment of weight (1005) locations relative to the device;

FIG. 31 is a schematic representation of a material of certain embodiments of the present invention. FIG. 31 shows a schematic polymer backbone structure of a hydrophobic material (1) and the addition of colour-forming molecules (2) to result in a solid dispersion that is either a molecular dispersion (3), consisting of isolated molecules of a colour-former (5) dispersed within the hydrophobic material structure (1), or a partial molecular dispersion (4), consisting of some isolated molecules of colour-former (5) and some isolated molecular clusters of colour-former (6) dispersed within the hydrophobic material structure (1);

FIG. 32 illustrates in cross-section a device (100) of certain embodiments of the invention for the measurement of the duration and direction of an applied shear force, comprising a first element (101) in which is dispersed a colour-forming dye in its uncoloured state and a second element (301) in which is immobilised a particulate colour developer. These two elements are spatially separated by a third element (310) upon which they are directly or indirectly associated. In the embodiment shown, a profiled circular perimeter of the second element (301) is associated directly with (310). In the centre of (310) is embedded a magnet (311) and this magnet is associated with a second magnet (312) upon which is mounted a profiled circle of the first element (101); and FIG. 33 is a cross-sectional view of the device illustrated in FIG. 32 when shear force is applied. FIG. 33A illustrates in cross-section a device (100) as shown in FIG. 32 with a shear force (315) acting in a direction parallel to the surface of the device in a left-to-right direction shown by the arrow. The action of this shear force displaces the magnet (312) and its associated first element (101) from its resting position, centred over magnet (311) in a direction aligned with the shear force. Above a predetermined shear force (dictated by the magnetic strength of the magnets (311) and (312) and the geometry of the device), the first element (101) contacts the second element (301) at the face (320) as depicted in FIG. 33B. At the contact face of the elements (101) and (301), colour former migrates from the first element (101) into the second element (301) and colour (325) is developed in a contact time-dependent manner in (301), as depicted in FIG. 33C. When the shear force ceases, the magnet (312) and its associated first element (101) returns to its resting position, centred over the magnet (311), as depicted in 33D. Contact between the elements (101) and (301) ceases and colour formation in the second element (301) ceases until a further shear event occurs. The circular format of this embodiment enables shear direction to be readily visualised from the location and intensity of the developed colour in the second element (301); and FIG. 34 is a cross-sectional representation of a certain embodiments of the invention for the measurement of the duration of applied pressure in applications where direct observation of the device by the user is not possible. The device described and shown in FIG. 10 (100) is used here as a non-limiting example of the following:

A pressure duration recording device (100) is positioned between two parallel and transparent rigid windows (2010) held at fixed spatial locations by spacing elements (1020). A first flexible bladder of largely two-dimensional geometry (1030) is positioned between the pressure recording device (100) and one of the rigid windows (2010). This first flexible bladder (1030) is in fluid communication with a second flexible bladder of largely two-dimensional geometry (1040) via a conduit (1050). The second flexible bladder (1040) is positioned at the site of interest (1060).

When a pressure is applied to the site of interest (1060), the second flexible bladder (1040) is compressed (for positive applied pressures) and this pressure is communicated to the pressure recording device (100) via the conduit (1050) and the first bladder (1030). In this manner, pressure durations at sites of interest can be made in the absence of a direct line of sight. Such locations may be internal sites or external sites covered by clothing or medical devices such as compression bandaging, stockings or wound dressings and suchlike.

A further advantage of the device of the embodiment shown in this Figure that the recording of pressure duration above a pre-determined threshold is insensitive to the geometry and topography of the site of interest.

DETAILED DESCRIPTION OF CERTAIN EMBODIMENTS OF THE INVENTION

In a first aspect of the present invention, there is provided a device for indicating a parameter, the device comprising an element comprising a hydrophobic material and a colour-forming material dispersed in at least a portion of the hydrophobic material.

Aptly, the parameter is as described herein and is for example, application of increased or reduced pressure and/or contact and/or shear to the device.

Thus, certain embodiments of the present invention comprise the use of a solid material in which is uniformly distributed one or more colour-forming materials, characterised in that the solid material allows the diffusion of the colour-forming material throughout its structure. Aptly, the solid material is hydrophobic.

In a further aspect of the present invention, there is provided a device comprising an element comprising a hydrophobic material and a colour-forming material dispersed in at least a portion of the hydrophobic material, wherein the element comprising the hydrophobic material and the colour-forming material dispersed in at least a portion of the hydrophobic material is a first element and wherein the device further comprises a second element, the second element comprising a colour developing material.

In a further aspect of the present invention, there is provided a device comprising an element comprising a hydrophobic material and a colour-forming material dispersed in at least a portion of the hydrophobic material, the element comprising the hydrophobic material and the colour-forming material dispersed in at least a portion of the hydrophobic material being a first element and wherein the device further comprises a second element, the second element comprising a colour developing material, and wherein the device further comprises a third element located to maintain the first element and the second element in a non-associated state until pressure greater than or less than a predetermined threshold is applied to the device. Details of the first element, the second element and the third element are provided herein. Aptly, the third element is a permanent e.g. non-removable feature of the device. Aptly, the first, second and/or third elements are each separable from each other and brought into contact in use. In one embodiment, the device may comprise more than one first element, second element and/or third element.

Aptly, the device comprises an element e.g. the first element which is a solid-state element. Aptly, the hydrophobic material is a solid material. Aptly, the hydrophobic material is capable of permitting diffusion of the colour-forming material through its structure. Aptly, the hydrophobic material has a hardness of between about 0 and 80 Shore OO e.g. 0, 10, 20, 30, 40, 50, 60, 70 or 80 Shore OO.

In one embodiment, the device comprises a plurality of elements comprising a hydrophobic material as described herein, each element being positioned in a discrete location, wherein each element comprises a colour forming material which is capable of forming a different colour when brought into contact with a colour developing material. The plurality of elements may be a plurality of first elements.

In an embodiment, the hydrophobic material may be any that allows the uniform distribution of colour former throughout its structure and also allows molecular diffusion of the colour former through its structure. Aptly, the solid material comprises a hydrophobic polymer. Aptly, the solid material comprises an elastomeric hydrophobic polymer.

Aptly, the solid material comprises a hydrocarbon-based gel. Aptly, the hydrocarbon based gel material comprises a hydrocarbon and a co-polymer. Aptly, the hydrocarbon based gel material comprises about 70% to about 98% by weight of a hydrocarbon, and up to about 30% by weight of a co-polymer selected from the group consisting of a triblock, radial block and multiblock copolymers, and optionally from 0 to about 10% by weight of a diblock copolymer.

Suitable hydrocarbon-based gels include for example those described in U.S. Pat. No. 6,066,329 (Pennzoil Products Company). These materials are owned and marketed by Calumet Penreco Inc. under the trade name Versagel. These materials are solids at 25° C. and pourable liquids at temperatures above 80° C. Materials of the Versagel C and Versagel R product ranges are all suitable for use as the solid material of certain embodiments of the invention. Aptly, the colour-forming material can be fully solubilised in the hydrocarbon gel at a temperature above the melting point of the hydrocarbon gel; cooling solidifies the gel.

In one embodiment, silicone based materials are also suited to the uniform distribution of colour-forming materials throughout their structure. Aptly, silicone based materials are commonly prepared from two solvent-free liquid pre-polymers, in to either or both of which materials can be distributed. The inventor has identified that several colour-forming materials can be dissolved by one or both of these solvent-free liquid pre-polymers, enabling the uniform distribution of the colour-forming material in the final polymerised product at the molecular level. This may have particular application for indicating contact-, shear- and pressure-duration as described herein.

Aptly, suitable silicone-based polymers include the Silastic range of silicone elastomers (Dow Corning Corp.) and the Elastosil (Silpuran) range of silicone elastomers (Wacker Chemie AG).

Aptly, the hydrophobic material is suitable for medical use (i.e. is a medical grade material).

Aptly, the hydrophobic material comprises between about 0.001% and 20% w/w of the colour-forming material, e.g. between about 0.01% and 10% w/w of the colour-forming material.

Aptly, the element is in the form of a sheet, e.g. a flexible sheet, a tube or a solid block. Aptly, the element is a first element.

Aptly, the element may be patterned and/or textured upon one or both of its surfaces. Aptly, the element may comprise one or more surface patterns e.g. a lined pattern and/or a grid pattern and/or a wave pattern. Aptly, the element may comprise one or more surface protrusions on one or both of its surfaces. The protrusion(s) may be provided in an ordered pattern or alternatively a random pattern. Aptly, the element is a first element.

Aptly, the element comprises a colour-forming material. Aptly, the element is a first element. Aptly, the colour forming material is substantially uniformly dispersed in the hydrophobic material.

As used herein, the terms "colour-forming material", "colour-forming species", "colour-forming dye" and "colour former" are interchangeable and are taken to relate to and/or comprise a molecule that can exist in at least two coloured states, one of which may be colourless. In one embodiment, the colour forming material is an organic molecule.

The colour-forming (CF) material can be of a size in the range of 10 μm diameter particulates down to individual molecules. Aptly, the CF material is uniformly distributed at the molecular level in the solid material. This may be termed as 'fully dissolved in' by the skilled artisan. This may also be described as a "solid dispersion" by the skilled artisan, including a "molecular dispersion" or a "partial molecular dispersion".

The colour-forming material e.g. the colour-forming species may be any known to the skilled artisan and may, for example, include: acyl auramines, acylleucophenothiazines, alpha- and beta-unsaturated aryl ketones, azaphthalides, basic mono azo dyes, 10-benzoyl-N,N,N',N'-tetraethyl-3,7-diamino-10H-phenoxazine, chromogenic azaphthalide compounds, diaryl phthalides, diphenylmethanes, dithio-oxamide, di[bis-(indolyl)ethylenyl]tetrahalophthalides, fluoran derivatives (3-dialkylamino-7-dialkylamylfluoran), 3-(indol-3-yl)-3-(4-substituted aminophenyl)phthalides, bis-(indolyl)ethylenes, indolyl red, leucoauramines, leucobenzoyl methylene blue, 3-methyl-2,2-spirobi(benzo-[f]-chromene), phenoxazine, phthalides including crystal violet lactone, malachite green lactone, phthalide red, phthalide violet, phthalans, benzoindolinospiropyrans, rhodamine beta lactams, spiropyrans, triphenylmethanes including gentian violet and malachite green.

The colour-forming species is aptly chosen from the following: leuco crystal violet [CAS 603-48-5], crystal violet lactone [CAS 1552-42-7], 7-Anilino-3-diethylamino-6-methyl fluoran [CAS 29512-49-0], 2-Anilino-6-dibutylamino-3-methylfluoran [CAS 89331-94-2], 3,3-bis(2-methyl-1-octyl-1H-indol-3-yl)-1(3H)-Isobenzofuranone [CAS 50292-95-0], N-ethyl-N-chloroethyl-3-toluidine [CAS 22564-43-8], N-ethyl-N-benzyl aniline-3'-sulfonic acid [CAS 101-11-1], 2-chlorobenzaldehyde oxime [CAS 3717-28-0], 6'-(diethylamino)-2'-[(dimethylphenyl)amino]-3'-methylspiro[isobenzofuran-1(3H),9'-[9H]xanthene]-3-one [CAS 72389-80-1], 3-(Ethylisoamylamino)-6-methyl-7-anilinofluoran [CAS 70516-41-5], 2'-(Dibenzylamino)-6'-(diethylamino)fluoran [CAS 34372-72-0], N,N-Dimethyl-4-[2-[2-(octyloxy)phenyl]-6-phenyl-4-pyridinyl]benzenamine [CAS 144190-25-0] or 4-[4-[4-[2-[4-[2-[4-(diethylamino) phenyl]quinazolin-4-yl]oxyphenyl]propan-2-yl]phenoxy] quinazolin-2-yl]-N,N-diethylaniline [CAS 90677-64-8], 3-(4-chloro-phenyl)-3-phenyl-3H-isobenzofuran-1-one; 10,10-dimethylspiro(anthracene-9(10H),1'(3'H)-isobenzofuran)-3'-one; 3-(2-(dimethylaminomethyl)phenyl)-3-phenylphthalide; (5,1',1',5")terisobenzofuran-1,3,3',1",3"-pentaone; 4-{1-[4-(benzoyloxy)phenyl]-3-oxo-1,3-dihydro-2-benzofuran-1-yl}phenyl benzoate; 3-(alpha-(4-chlorophenyl)-2-(dimethylamino)benzyl)-3-methylphthalide; o-Cresolphthalein Complexone [2411-89-4]; Fluorescein diacetate [596-09-8]; Naphthofluorescein [61419-02-1]; Fluorescein O,O'-diacrylate [7262-39-7]; Fluorescein o-acrylate [193419-86-2]; 5-Carboxyfluorescein diacetate [79955-27-4]; 3',6'-dichlorofluoran [630-88-6]; Rhodol [3086-44-0]; Fluorescein O,O'-dimethacrylate [206444-58-8]; Fluorescein O-methacrylate [480439-15-4]; Fluorescein dibutyrate [7298-65-9]; Fluorescein dilaurate [7308-90-9]; 2',7'-Dichlorofluorescein diacetate [2044-85-1]; Fluorescein diacetate 6-isothiocyanate; Rose Bengal diacetate [61738-01-0]; 3,4-diamino-9-(2-carboxyphenyl)-3,6-bis(diethylamino)xanthenium chloride, DAR-2 [261351-45-5]; 4,5-diamino-9-(2-carboxyphenyl)-3,6-bis (diethylamino)xanthenium chloride, DAR-1 [261351-43-3]; Eosin Y [15086-94-9]; Erythrosin B [15905-32-5]; Calcein [1461-15-0]; 4-nitrofluorescein [14926-29-5]; 2',7'-bis(2-Carboxyethyl)-5(6)-carboxyfluorescein acetoxymethyl ester Mixed isomers [117464-70-7]; Rose Bengal lactone [4159-77-7]; 2',4',5',7'-tetrabromo-3,4,5,6-tetrachlorofluorescein; Eosin diacetate [7284-92-6]; 5(6)-Carboxy-2',7'-dichlorofluorescein diacetate [127770-45-0]; 5(6)-Carboxyeosin diacetate [161338-87-0]; 5(6)-Carboxytetramethylrhodamine N-hydroxysuccinimide ester; Fluorescein Phosphoramidite; 6-FAM(R) [204697-37-0]; ZnAF-1 DA; 5(6)-Carboxyfluorescein diacetate N-succinimidyl ester [150347-59-4]; 5(6)-Carboxy-X-rhodamine [198978-94-8] or a composition thereof. The colour-forming species is also aptly chosen from those listed at paragraph [0022] of US2007/0207925, the contents of which are incorporated herein by reference in their entirety.

Aptly, the colour-forming species is a phthalide-based leuco dye selected from the following: crystal violet lactone [CAS 1552-42-7], 6-diethylamino-3-methyl-2-phenylaminofluoran [CAS 29512-49-0], 2-Anilino-6-dibutylamino-3-methylfluoran [CAS 89331-94-2], 6-(N-ethyl, N-isopentylamino)-3-methyl-2-phenylaminofluoran [CAS 70516-41-5], 2-(dibenzylamino)-6-(diethylamino)fluoran [CAS 34372-72-0], 2-(2,4-dimethylphenylamino)-3-methyl-6-diethylaminofluoran [CAS 72389-80-1], 3,3-bis(N-octyl-2-methyl indole)phthalide [50292-95-0], 4,4'-[(1-methylethylidene)bis(4,1-phenyleneoxy-4,2-quinazolinediyl)]bis[N,N-diethyl]benzamine [CAS 90677-64-8] and the colour-forming species shown in Example 1 of US2007/0207925 labelled CF1-CF17.

Aptly the colour-forming species is a phthalide-based leuco dye chosen from the following: crystal violet lactone [CAS 1552-42-7], 2-(dibenzylamino)-6-(diethylamino)fluoran [CAS 34372-72-0], 2-(2,4-dimethylphenylamino)-3-methyl-6-diethylaminofluoran [CAS 72389-80-1], 3,3-bis (N-octyl-2-methyl indole)phthalide [50292-95-0] and 4,4'-[(1-methylethylidene)bis(4,1-phenyleneoxy-4,2-quinazolinediyl)]bis[N,N-diethyl]benzamine [CAS 90677-64-8].

Aptly, the colour forming molecules are incorporated into the device of certain embodiments of the present invention in a colourless state.

Aptly, the element comprises more than one colour forming material. When more than one colour-former is used, the differential diffusion rates of the colour formers through the solid material can by utilised to generate multi-coloured transitions over time during contact, subsequent to initial colour-formation from a colourless state. As shown in Example 8, more than one colour can be formed from a single hydrophobic material. Aptly, the hydrophobic material comprises two or more colour forming materials. Aptly, each colour forming material has a distinct diffusion rate through the hydrophobic material. Thus, the faster diffusing colour forming material will be the predominant colour at shorter durations and the observed colour will then be modified by the slower diffusing colour forming material at longer durations.

The colour forming material may be loaded into the solid material at a level in the range of 0.001-20% w/w. Aptly, the colour former may be loaded into the solid material at a level in the range of 0.1-10% w/w. Aptly, the colour forming material is substantially completely dissolved in the hydrophobic material. Aptly, the colour forming material dissolved within the hydrophobic material can be characterised as a solid dispersion. This solid dispersion may be a molecular dispersion or partial molecular dispersion, see FIG. 31.

Aptly, the device comprises a plurality of elements comprising a hydrophobic material and a colour forming material, each element being provided in a discrete location. Each element may be spaced apart from every other element comprising a colour forming material.

In one embodiment, the element comprising the hydrophobic material and the colour-forming material dispersed in at least a portion of the hydrophobic material is a first element and wherein the device comprises a second element, the second element comprising a colour developing material.

In a further aspect of the present invention, there is provided a device comprising an element comprising a hydrophobic material and a colour-forming material dispersed in at least a portion of the hydrophobic material, wherein the element comprising the hydrophobic material and the colour-forming material dispersed in at least a portion of the hydrophobic material is a first element and wherein the device further comprises a second element, the second element comprising a colour developing material.

Aptly, the second element of various aspects of the present invention is a solid-state element. Aptly, the second element comprises a hydrophobic material, and the colour developing material is substantially uniformly dispersed in at least a portion thereof.

In an embodiment, the hydrophobic material of the second element is a silicone-based material. In one embodiment, the hydrophobic material is a hydrocarbon-based gel material.

Aptly, the second element comprises a layer composed of the colour developing material.

Aptly, the colour developing material is a particulate.

As used herein, the terms "colour developer" and "colour developing material" are interchangeable and include a species that, when in intimate contact with a colour-forming material in its colourless state, converts the colour forming material to a coloured state.

The colour developer is aptly immobilised within or on the surface of the second element and cannot diffuse or otherwise escape from its location. For this purpose, aptly the colour developer is incapable of diffusion through the solid material of which the second element is constructed. It is desirable for the colour developer to be provided in the form of a powder of particle size in the range 10 nm-1 mm. When the colour developer is a clay or ceramic powder, particle morphology may be any known such as platelet, spheroid or needle.

The colour developer may be any known to the skilled artisan and may, for example, include: acidic clay, montmorillonite clay, activated clay, alumina, silica or silica gel, aluminium sulphate, aluminium phosphate, attapulgite, bentonite, acid-activated bentonite, calcium stearate, kaolin, halloysite, zeolite, zinc chloride, zinc nitrate, lauryl gallate, gallic acid, maleic acid, malonic acid, succinic acid, bisphenol A, salicylic acid, sulfosalicylic acid, substituted salicylic acids, phenol and substituted phenols.

Aptly the colour developer is a clay or a phenolic resin. Aptly, the colour developer is bentonite or acid-activated bentonite.

In one embodiment, the second element comprises a Fuji Prescale C-Film (Fuji Photo Film Co., Ltd.). In one embodiment, the second element comprises a solid ceramic surface (i.e. is comprised entirely of colour developer).

Aptly, the second element of the device is constructed of any material enabling the uniform dispersion of the colour developer, including a material constructed entirely of a colour developer. The dispersion may be a surface coating or a bulk impregnation. If the second element contains the colour developer within its bulk, aptly it is constructed of a material that allows the diffusion of colour former molecules through its structure. Aptly, when the colour developer is dispersed in the bulk of the second element, the second element is constructed of the same material as the first element: e.g. a silicone-based polymer or a hydrocarbon based gel, as described herein.

Suitable silicone-based polymers include for example the Silastic range of silicone elastomers (Dow Corning Corp.) and the Elastosil range of silicone elastomers (Wacker Chemie AG).

Aptly, the device comprises a first element in which is dispersed a colour-forming dye in its uncoloured state, and a second element in which is immobilised a particulate colour developer, characterised in that both the first element and second element are constructed of a solid material that allows the diffusion of the colour-forming dye but not the colour developer.

Aptly, colour forms substantially exclusively within the second element and the second element may be semi-transparent due to the presence of colour developer particles. Aptly, the thickness of the second element is less than about 5 mm to facilitate direct viewing of colour development at or near contact points.

Aptly, the first and/or the second element is in the form of a sheet, e.g. a flexible sheet, a tube or a solid block.

Aptly, the first and/or the second element is produced in the form of discrete patches on a continuous sheet. This arrangement may be advantageous for the automated manufacture of the final device shown in FIG. 9. Production of discrete patches on a continuous sheet can be achieved using a silk-screen printing technique or a patch coating machine. If a silk screen technique is used, an automated reel-to-reel machine is apt.

Aptly, the element may be patterned and/or textured upon one or both of its surfaces. Aptly, the element may comprise one or more surface patterns for example, a lined pattern and/or a grid pattern and/or a wave pattern. Aptly, the element may comprise one or more surface protrusions on one or both of its surfaces. The protrusion(s) may be provided in an ordered pattern or a random pattern.

In use, the first element is brought into contact with the second element and colour develops in the second element only where contact occurs. The colour intensity is related to the duration of contact in a predictable manner.

Aptly, the first element comprises a first face and a second face. Aptly, the second element comprises a first face and a second face. In one embodiment, the first element comprises a plurality of protrusions on the first face and/or the second face. Aptly, the second element comprises a plurality of protrusions on the first face and/or the second face. Aptly, the protrusions allow contact between about 5% to 95% of the surface area of the elements when they are brought into contact e.g. approximately 10%, 20%, 30%, 40%, 50%, 60%, 70%, 80% or 90%. Protrusions on the face acting as a contact surface of one or both elements enable the focus and amplification of an applied pressure by effectively reducing the contact area through which the applied pressure can act. In this way, the devices and apparatus of certain embodiments of the present invention may overcome the low-pressure threshold limitations of existing pressure mapping devices.

Aptly, the device comprises a third element located to maintain the first element and the second element in a non-associated state until pressure greater than or less than a predetermined threshold value is applied to the device.

Aptly, the third element is located between the first element and the second element. Aptly, a surface of the third element is in direct contact with a surface of one or both of the first and second elements.

The third element may be constructed of any material and may be a gas, liquid or solid. Aptly, the material of construction of the third element is non-reactive and is impermeable to the colour-forming dye. The third element may be constructed in any geometry provided that it enables the first element and second element to contact one another, at least in part, when a topical pressure is applied to or removed from the device.

Aptly, the third element comprises one or more apertures. Aptly, the apertures are sized to permit contact to occur between the first and second elements of the device and the colour forming material to diffuse from the first element to the second element at the contact areas when a pressure above or below a predetermined threshold pressure is applied to or removed from the device. In certain embodiments, the third element comprises a plurality of apertures and the device is for the detecting and/or measurement of pressure.

In one embodiment, the third element is a spacer and the device is for measuring and/or detecting generation of contact.

Aptly, the third element may be constructed of a woven, non-woven or knitted material or an otherwise apertured (e.g. perforated or slit and extended) continuous material. When the third element is a woven or knitted material, it is aptly constructed of a monofilament yarn.

Non-limiting examples of apertured materials include the woven and knitted materials of Harrington Fabric and Lace (Nottingham, England) including item numbers: 4924, 4926 and 4917 and the bobbinet materials of Swisstulle UK Ltd (Nottingham, England) including article numbers: 182/28, 186, 188 and 198.

In one embodiment, the first element and the second element are located in a spaced apart relationship. Aptly, a surface of the first element and a surface of the second element are brought into contact when the device is perturbed such that colour is formed in the second element at the site of contact. Alternatively, the first element and the second element are located in a spaced apart relationship and the device comprises a third element, wherein when the device is perturbed, the colour forming material diffuses through the third element such that colour is formed in the second element. Aptly, this third element comprises a material which is substantially permeable to the colour forming material.

In one embodiment, the device is for detecting application and/or duration of shear force. Aptly, the first element comprises a magnetic element. Aptly, the second element comprises a corresponding magnetic element. The magnetic elements hold the first and second elements in a predetermined spatial arrangement in which the first and second elements do not contact each other. Aptly, when a shear force of a predetermined threshold value is applied to the first element, contact between the magnetic elements is weakened and the first element is moved towards the second element in the direction of the applied shear force. Thus, aptly, application of the shear force results in contact of the first element and the second element. Aptly, the colour forming material of the first element diffuses into the second element such that colour is formed in the second element. Thus, in certain embodiments, the device may be used to indicate the duration and direction of the application of a shear force. Aptly, the device comprises more than one first elements, second elements and/or third elements.

In one embodiment, the device is column-shaped. Aptly, the first element is a sheet e.g. a flexible sheet.

Aptly, the second element is a sheet e.g. a flexible sheet. Aptly, the third element is a sheet e.g. a flexible sheet.

In one embodiment, the device is a tube and comprising a through channel.

Aptly, the first element and/or the second element is substantially transparent.

Aptly, the first element and/or the second element is semi-transparent. Aptly the third element is substantially transparent, semi-transparent or opaque.

In one embodiment, the device further comprises an upper layer and a lower layer which are capable of forming an envelope enclosing the first element, the second element and optionally the third element.

Aptly, the device comprises an aperture for communicating with a vacuum source. Aptly, the device comprises a port for attaching a vacuum source. Aptly, the device is for detecting application and/or duration of application of a vacuum i.e. application of negative pressure. The negative pressure may be applied continuously or non-continuously. The negative pressure may have a value of between about −50 and −200 mmHg e.g. between about −75 to −125 mmHg.

In one embodiment, the device further comprises an adhesive layer.

In a further aspect of the present invention, there is provided a kit comprising a device as described herein and a calibrated colour chart, wherein the kit is for measuring cumulative contact and/or pressure duration.

Aptly, when the device is largely two dimensional and each of the three elements is constructed in flat sheet form, the third element may be constructed of a woven, non-woven or knitted material or an otherwise apertured (e.g. perforated or slit and extended) continuous material. When the third element is a woven or knitted material, it is aptly constructed of a monofilament yarn.

The geometry (both aperture and yarn size) of the third element aptly allow at least 20% of the surface area of the first and second elements to contact one another above the pressure threshold of the device. More aptly, the geometry of the third element aptly allows at least 50% of the surface area of the first and second elements to contact one another above the pressure threshold of the device.

Aptly, the geometry of the third element is relatively insensitive to macroscopic distortions in device geometry. Individual aperture area may lie within the range 0.01-100 mm$^2$.

Aptly, the third element is a woven net with apertures such as square or rectangular or hexagonal apertures. Aptly, the woven net has square apertures and has a mesh size in the range of 9-10000 apertures (or 6-200 filaments) per square centimeter and filament diameter in the range 0.001-1 mm.

A further aspect of the present invention provides apparatus for the measurement of cumulative contact duration and its distribution comprising a device as described herein and a calibrated colour chart to enable the determination of the cumulative duration of contact and its distribution.

A further aspect of the present invention provide apparatus for the measurement of cumulative applied pressure duration and its distribution comprising a device as described herein and a calibrated colour chart to enable the determination of the cumulative duration of applied pressure and its distribution.

A further aspect of the present invention provide apparatus for the measurement of cumulative shear duration and its direction comprising a device as described herein and a calibrated colour chart to enable the determination of the cumulative duration of applied shear and its distribution.

In a yet further aspect of the present invention, there is provided a method of making a device as described herein, which comprises:
a) uniformly dispersing a colour forming material in a liquid polymer; and
b) cooling the polymer to its solid state.

Aptly the method is for making a first element of a device as described herein.

In a yet further aspect of the present invention, there is provided a method of making a device as described herein, which comprises:
a) uniformly dispersing a colour developing material in a liquid polymer; and
b) cooling the polymer to its solid state.

Aptly the method is for making a second element of a device as described herein.

In a yet further aspect of the present invention, there is provided a method of making a device as described herein, which comprises:
a) uniformly dispersing a colour forming material in a liquid polymer;
b) cooling the polymer to its solid state;
c) forming a first element of the device;
d) uniformly dispersing a colour developing material in a liquid polymer; and
e) cooling the polymer to its solid state; and
f) forming a second element of the device.

In a yet further aspect of the present invention, there is provided a method of making a device as described herein, which comprises:
a) uniformly dispersing a colour forming material in a pre-polymer liquid; and
b) curing the pre-polymer liquid to a solid polymer.

Aptly, the pre-polymer liquid is a silicone-based pre-polymer liquid. Aptly, the pre-polymer liquid is a two-part silicone based pre-polymer liquid and the method comprises mixing the two-part silicone based pre-polymer liquid prior to curing. Aptly, curing the pre-polymer liquid comprises using a platinum based catalyst.

Uniform dispersion of the colour former in a silicone-based pre-polymer can be achieved by any means known to the skilled artisan, e.g. high- or low-shear mechanical mixing. It has been determined that the colour formers identified above readily dissolve in the silicone-based pre-polymer and remain fully dissolved during the curing process which may be a heat or light-triggered process.

Aptly, the process includes two-part silicone-based pre-polymers that require mixing prior to curing to generate the desired silicone-based polymer. In this case, the colour former may be dispersed in one or both of the pre-polymer components prior to mixing. Aptly, these two part systems comprise of a low molecular weight silicone prepolymer (Part A) and a functionalised chain-extending silicone pre-polymer including a catalytic platinum complex initiator (Part B).

In a further aspect of the present invention, there is provided a method of indicating contact, comprising locating a device as described herein in a target location and detecting a colour change of the colour forming material.

In a further aspect of the present invention, there is provided a method of indicating shear, comprising locating a device as described herein in a target location and detecting a colour change of the colour forming material.

In a further aspect of the present invention, there is provided a method of indicating application or removal of pressure, comprising locating a device as described herein in a target location and detecting a colour change of the colour forming material.

Aptly, the method is for detecting when a pressure applied to or removed from the device exceeds or falls below a predetermined threshold value. In one embodiment, the method is for detecting the application of a negative pressure to the device.

In one embodiment, the method is for detecting the non-continuous application or removal of pressure to the device.

Aptly, the method is for indicating a pressure level applied to a portion of a human body.

Aptly, the method is for indicating a pressure level applied to a topical device (e.g. drug delivery patch or wound dressing or pressure off-loading device) positioned upon a portion of a human body.

In one embodiment, the method is for indicating the non-continuous application or removal of a shear force to the device.

Aptly, the method is for indicating a shear force applied to a portion of a human body.

Aptly, the method is for indicating a shear force applied to a topical device (e.g. drug delivery patch or wound dressing or pressure off-loading device) positioned upon a portion of a human body.

Aptly, the method is for the prevention or reduction of pressure sore formation on a human or animal body.

Aptly, the method is for monitoring a vacuum pressure level being applied to a wound or other surgical site on a human body. The vacuum pressure level may be between about 0 to −1000 mmHg, e.g. about −50 mmHg to about −200 mmHg, e.g. −75 mmHg to about −125 mmHg.

Aptly, the device changes colour when the pressure applied to the device exceeds or falls below a predetermined threshold value.

Aptly, the device changes colour when the shear applied to the device exceeds or falls below a predetermined threshold value.

In one embodiment, the method comprises detecting the application of pressure over a predetermined period of time, for example, one hour, two hours, three hours, four hours, five hours, six hours, seven hours, eight hours or more e.g. twelve hours, twenty-four hours or a period of several days.

In one embodiment, the method comprises detecting the application of shear over a predetermined period of time, for example, one hour, two hours, three hours, four hours, five hours, six hours, seven hours, eight hours or more e.g. twelve hours, twenty-four hours or a period of several days.

In one embodiment, the method is for monitoring the presence of ceramic dust in an environment surrounding the device. Aptly, the method comprises detecting a colour change when a ceramic dust particle contacts the hydrophobic material.

In one embodiment, the device is a ceramic dust monitor. In this embodiment, the hydrophobic material comprising the colour forming material is a tape for mounting on a surface or on a badge for personal use. When a ceramic particle contacts the surface, colour is developed in contact with the particle. The ceramic particle acts as a colour developing material as described herein.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

There now follows a series of specific embodiments of the invention. These specific embodiments do not restrict the scope of the invention.

EXAMPLES

Example 1

Preparation of Silicone Elastomer Containing a Uniform Concentration of Crystal Violet Lactone (0.5% w/w), a Blue Colour-Former Crystal violet lactone powder (50 mg) was added to Silpuran 2420/30 Part A liquid, 5 g (Wacker Chemie AG) and mixed by hand using a spatula until homogeneous distribution was achieved. The part-solubilisation of the crystal violet lactone could be observed by the greying of the liquid; full solubilisation was not achieved at this stage. To this homogeneous mixture was added Silpuran 2420/30 Part B liquid, 5 g (Wacker Chemie AG) and the components intimately mixed by hand using a spatula. Further solubilisation of the crystal violet lactone occurred. The homogeneous mixture was spread on acetate sheet using a hand spreading block with a 760 micron slit height. The crystal violet lactone was fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a very slight blue tint.

Example 2

Preparation of Silicone Elastomer Containing a Uniform Concentration of 2-dibenzylamino-6-diethylaminofluoran (0.5% w/w), a Green Colour-Former WinCon Green powder, 50 mg (Connect Chemicals GmbH) was added to Silpuran 2420/30 Part A liquid, 5 g (Wacker Chemie AG) and mixed by hand using a spatula until homogeneous distribution was achieved. The part-solubilisation of the colour-former could be observed by the greying of the liquid; full solubilisation was not achieved at this stage. To this homogeneous mixture was added Silpuran 2420/30 Part B liquid, 5 g (Wacker Chemie AG) and the components intimately mixed by hand using a spatula. Further solubilisation of the colour-former occurred. The homogeneous mixture was spread on acetate sheet using a hand spreading block with a 760 micron slit height. The colour-former was fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a very slight green tint.

Example 3

Preparation of Silicone Elastomer Containing a Uniform Concentration of 2-(2,4-dimethylphenylamino)-3-methyl-6-diethylaminofluoran (0.5% w/w), a Black Colour-Former WinCon-15 powder, 50 mg (Connect Chemicals GmbH) was added to Silpuran 2420/30 Part A liquid, 5 g (Wacker Chemie AG) and mixed by hand using a spatula until homogeneous distribution was achieved. The part-solubilisation of the colour-former could be observed by the greying of the liquid; full solubilisation was not achieved at this stage. To this homogeneous mixture was added Silpuran 2420/30 Part B liquid, 5 g (Wacker Chemie AG) and the components intimately mixed by hand using a spatula. Further solubilisation of the colour-former occurred. The homogeneous mixture was spread on acetate sheet using a hand spreading block with a 760 micron slit height. The colour-former was fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a very slight red tint.

Example 4

Preparation of Silicone Elastomer Containing a Uniform Concentration of 3,3-bis(n-octyl-2-methyl indole)phthalide (0.5% w/w), a Red Colour-Former WinCon Red powder, 50 mg (Connect Chemicals GmbH) was added to Silpuran 2420/30 Part A liquid, 5 g (Wacker Chemie AG) and mixed by hand using a spatula until homogeneous distribution was achieved. The part-solubilisation of the colour-former could be observed by the greying of the liquid; full solubilisation was not achieved at this stage. To this homogeneous mixture was added Silpuran 2420/30 Part B liquid, 5 g (Wacker Chemie AG) and the components intimately mixed by hand using a spatula. Further solubilisation of the colour-former occurred. The homogeneous mixture was spread on acetate sheet using a hand spreading block with a 760 micron slit height. The colour-former was fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a red tint.

Example 5

Preparation of Silicone Elastomer Containing a Uniform Concentration of 4,4'-[(1-methylethylidene)bis(4,1-phenyleneoxy-4,2-guinazolinediyl)]bis [N,N-diethyl]benzamine (0.5% w/w), a Yellow Colour-Former Pergascript Yellow I 3R powder, 50 mg (Connect Chemicals GmbH) was added to Silpuran 2420/30 Part A liquid, 5 g (Wacker Chemie AG) and mixed by hand using a spatula until homogeneous distribution was achieved. No solubilisation of the colour-former could be observed at this stage. To this homogeneous mixture was added Silpuran 2420/30 Part B liquid, 5 g (Wacker Chemie AG) and the components intimately mixed by hand using a spatula. Part-solubilisation of the colour-former occurred. The heterogeneous but uniformly dispersed mixture was spread on acetate sheet using a hand spreading block with a 760 micron slit height. The spread sheet was placed in an oven at 70° C. for 20 minutes to cure the silicone to an elastomeric solid of approximately 30 Shore OO hardness. The product was fully transparent but with visible particulates and was colourless.

Example 6

Preparation of Silicone Elastomer Containing a Uniform Concentration of Crystal Violet Lactone (0.5% w/w) and 3,3-bis(N-octyl-2-methyl indole)phthalide (0.5% w/w), a Blue Colour Former and a Red Colour Former Crystal violet lactone powder, 50 mg, and WinCon Red, 50 mg (Connect Chemicals GmbH) was added to Silpuran 2420/30 Part A liquid, 5 g (Wacker Chemie AG) and mixed by hand using a spatula until homogeneous distribution was achieved. The part-solubilisation of the colour-formers could be observed by the greying of the liquid; full solubilisation was not achieved at this stage. To this homogeneous mixture was added Silpuran 2420/30 Part B liquid, 5 g (Wacker Chemie AG) and the components intimately mixed by hand using a spatula. Further solubilisation of the colour-formers occurred. The homogeneous mixture was spread on acetate sheet using a hand spreading block with a 760 micron slit height. The colour-formers were fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a red tint.

Example 7

Demonstration of Colour-Forming Ability of Devices Produced in Examples 1, 2, 4 and 5

2×2 cm squares of each of the sheet materials produced in Examples 1, 2, 4 and 5 were cut by mechanical press. The acetate backing sheet was left in place for ease of handling. Each sample was placed, exposed silicone side-down onto a sheet of Fuji Prescale C-Film. The colour intensity of each sample was recorded at the appropriate light absorbance wavelength over several hours (FIG. 18) and days (FIG. 19). The light absorbance was recorded using a UV-vis spectrometer with integrating sphere attachment (Avantes Avaspec 2048). The resulting light absorbances are tabulated below and represented graphically in FIGS. 18 and 19.

|  | WinCon Red (538 nm) | WinCon Green (585 nm) | WinCon Yellow (452 nm) | Crystal Violet Lactone (610 nm) |
| --- | --- | --- | --- | --- |
| Day |  |  |  |  |
| 0 | 0.304 | 0.171 | 0.046 | 0.129 |
| 1 | 0.974 | 0.621 | 0.329 | 0.715 |
| 2 | 0.991 | 0.715 | 0.435 | 0.816 |
| 3 | 0.96 | 0.786 | 0.482 | 0.828 |
| 4 | 0.963 | 0.834 | 0.51 | 0.855 |
| 5 |  | 0.922 | 0.487 | 0.874 |
| 6 | 0.961 | 0.936 | 0.501 | 0.873 |
| Hour |  |  |  |  |
| 0 | 0.304 | 0.171 | 0.046 | 0.129 |
| 1 | 0.698 | 0.289 | 0.219 | 0.233 |
| 2 | 0.822 | 0.357 | 0.255 | 0.288 |
| 3 | 0.864 | 0.391 | 0.268 | 0.318 |
| 4 | 0.918 | 0.43 | 0.285 | 0.352 |
| 5 | 0.946 | 0.466 | 0.298 | 0.376 |
| 6 | 0.967 | 0.491 | 0.305 | 0.396 |
| 24 | 0.974 | 0.621 | 0.329 | 0.715 |

The results demonstrate that the different colour-forming species diffuse from the silicone elastomer at different rates, dependent upon their molecular structure. The rates of diffusion are in the order:
WinCon Red>Crystal Violet Lactone≈WinCon Green>WinCon Yellow It should be noted however that WinCon Yellow failed to fully dissolve in the silicone elastomer and so might be expected to be available at lower concentrations than the other colour-formers. Notwithstanding this, for applications requiring rapid reporting of contact or pressure duration, of the order of a few minutes, WinCon Red may be a suitable colour former (if reporting colour is unrestricted in the chosen application). It was also found that WinCon-15 (a black colour-former, see Example 3) developed colour at a rate similar to WinCon Red.

Example 8

Demonstration of Colour-Forming Ability of a Colour-Former Mixture

2×2 cm squares of the sheet material produced in Example 6 was cut by mechanical press. The acetate backing sheet was left in place for ease of handling. The sample was placed, exposed silicone side-down onto a sheet of Fuji Prescale C-Film. The colour intensity of the sample was recorded at the appropriate light absorbance wavelength for each colour-former over several hours (FIG. 20) and days (FIG. 21). The light absorbances were recorded using a UV-vis spectrometer with integrating sphere attachment (Avantes Avaspec 2048). The resulting light absorbances are represented graphically in FIGS. 20 and 21.

The results correspond well with those observed for the component colour-formers when presented individually (see Example 7), so demonstrating that their different diffusion rates are maintained in the presence of one-another. The differential diffusion rates of different colour-formers has utility because it can be used to generate colour variation (in addition to transformation from colourless) correlated with contact time. Here, the colour transformation is from colourless to red within a matter of minutes-hours and then from red to purple over hours-days. FIG. 22 illustrates the relationship between the ratio of red (538 nm) and blue (610 nm) colour formation with time and shows the contribution of each species to the observed colour over time.

Example 9

The Effect of Differing Hydrophobic Materials on the Diffusion Rate of a Colour Forming Material In Examples 7 and 8, the differential diffusion rates of a range of colour formers through the same silicone-based elastomeric solid were demonstrated. In this example, the effect of variation in the chemistry of the silicone-based elastomer on the diffusion of a single colour former was investigated.

The method described in Example 1 was repeated for two other silicone elastomer formulations: Silpuran 2120 (an adhesive formulation) and Silpuran 2400/25. The materials produced contained 0.5% w/w crystal violet lactone.

2×2 cm squares of each of the sheet materials so produced cut by mechanical press. The acetate backing sheet was left in place for ease of handling. Each sample was placed, exposed silicone side-down onto a sheet of Fuji Prescale C-Film. The colour intensity of each sample was recorded at 610 nm over several hours. The light absorbance was recorded using a UV-vis spectrometer with integrating sphere attachment (Avantes Avaspec 2048). The resulting light absorbances are represented graphically in FIG. 23. The same colour former, when dispersed at the same concentration in different silicone elastomers, diffuses through their structures and from their surfaces at differing rates. Thus, the chemistry of the hydrophobic material can be used to tune the rate of diffusion of a given colour former.

It is also noted that the diffusion rate observed in this example for the softest silicone elastomer (Silpuran 2120) was slower than that from either of the other harder formulations and this is likely to be due to this adhesive formulation having a higher degree of cross-linking in its structure. It is hypothesised that small changes in the quantity of cross-linking prepolymer (prepolymer with 3 or more reactive ends) influences upon the rate of colour-former diffusion through the cured polymer.

Example 10

Demonstration of Colour-Forming Reproducibility

The material produced in Example 1 was studied as in Example 7 in triplicate. The resulting light absorbances are represented graphically in FIG. 24 and demonstrate the reproducibility of colour formation in this material when exposed to a colour developer.

Example 11

Preparation of Silicone Elastomer Containing a Uniform Dispersion of Bentonite (10% w/w), a Colour-Developer Bentonite powder (1 g) was added to Silpuran 2420/30 Part A liquid, 5 g (Wacker Chemie AG) and mixed by hand using a spatula until homogeneous distribution was achieved. To this homogeneous mixture was added Silpuran 2420/30 Part B liquid, 5 g (Wacker Chemie AG) and the components intimately mixed by hand using a spatula. The homogeneous mixture was spread on acetate sheet using a hand spreading block with a 760 micron slit height. The bentonite was completely insoluble in the silicone prepolymer. The spread sheet was placed in an oven at 70° C. for 20 minutes to cure the silicone to an elastomeric solid of approximately 30 Shore OO hardness. The product was translucent and allowed the transmission of light across its thickness.

Example 12

Preparation of a Device for the Measurement of Intermittent Pressure

In Example 7, the colour-forming ability of several colour formers dispersed in a silicone elastomer was demonstrated using a commercially available sheet-form colour developer. This format of colour developer is suitable for single-contact events. However, Fuji Prescale C-Film may not be suitable in combination with the materials as described herein when used for the measurement of intermittent contact events because these elements adhere to each other too strongly to enable easy or timely disconnection in use. Thus, an alternative colour developer layer was formulated and described in Example 11.

When the sheet formats described in any of Examples 1-6 are brought together with the sheet format described in Example 11, colour formation occurs at the same or similar rate to that observed in Examples 7 and 8. When the materials are separated, colour development ceases until the materials are brought together once again.

To construct a device as described herein, 50×50 mm squares of the materials otherwise prepared as described in Examples 4 and 11 were positioned centrally, with edges aligned, and on opposing faces of an 80×80 mm square of monofilament woven with 36 apertures per square centimeter and an open area of 85%. An 80×80 mm square sheet of polypropylene film of 30 micron thickness was placed centrally, with edges aligned, upon the remaining open face of each silicone elastomer and 10 mm edge weld was applied to the full perimeter of the construction, trapping the elastomeric sheets in place centrally. FIG. 9 illustrates this process.

An adhesive coating was applied to one face of this construction, suitable for application to a human body.

Example 13

Human Evaluation of the Cumulative Pressure-Duration Recording Device Described in Example 12

Four devices as described in Example 12 were prepared and adhered to: the right abdomen (2000), the left shoulder (2010), the right buttock (2020) and under the left heel (2030), see FIG. 25, of a healthy human volunteer. The devices were observed over 24 hours for the development of red colouration.

The device placed under the heel became completely red after 15 minutes.

The device placed on the buttock became completely red following a duration of 15 minutes in the seated position.

The device placed on the shoulder became completely red following a duration of 15 minutes while lying on this shoulder in a bed.

The device placed on the abdomen did not become red during this observation period.

It was concluded that this device would be suitable for the indication of applied pressures of a magnitude generated locally by an average adult human when standing, sitting or lying on hard or soft furnishings for 10-15 minutes.

Example 14

Preparation of a Device for the Measurement of Intermittent Pressure

50×50 mm squares of the materials otherwise prepared as described in Examples 4 and 11 were positioned centrally, with edges aligned, and on opposing faces of an 80×80 mm square of monofilament woven with 256 apertures per square centimeter and an open area of 64%. An 80×80 mm square sheet of polypropylene film of 30 micron thickness was placed centrally, with edges aligned, upon the remaining open face of each silicone elastomer and 10 mm edge weld was applied to the full perimeter of the construction, trapping the elastomeric sheets in place centrally. FIG. 9 illustrates this process.

An adhesive coating was applied to one face of this construction, suitable for application to a human body.

Example 15

Human Evaluation of the Cumulative Pressure-Duration Recording Device Described in Example 14

Four devices as described in Example 14 were prepared and adhered to: the right abdomen (2000), the left shoulder (2010), the right buttock (2020) and under the left heel (2030), refer to FIG. 25, of a healthy human volunteer. The devices were observed over 24 hours for the development of red colouration.

The device placed under the heel became completely red after 15 minutes.

The device placed on the buttock became completely red following a duration of 15 minutes in the seated position on a hard surface but not a cushioned surface.

The device placed on the shoulder became completely red following a duration of 15 minutes while lying on this shoulder against a hard surface but not a cushioned surface.

The device placed on the abdomen did not become red during this observation period.

It was concluded that this device would be suitable for the indication of applied pressures of a magnitude generated locally by an average adult human when sitting or lying on hard but not soft surfaces for 10-15 minutes (c.f. Example 13).

Example 16

Preparation of Versagel R1600 Containing a Uniform Concentration of Crystal Violet Lactone (1.0% w/w), a Blue Colour-Former Crystal violet lactone powder (50 mg) was added to Versagel R1600 liquid (5 g), heated to 100° C. Full solubilisation was achieved with mixing within 10 minutes. The homogeneous mixture was spread on polyester sheet using a hand spreading block with a 760 micron slit height. The product was fully transparent with no visible particulates and was colourless.

Example 17

Preparation of Versagel R1600 Containing a Uniform Concentration of 2-dibenzylamino-6-diethylaminofluoran (0.5% w/w), a Green Colour-Former WinCon Green powder (50 mg) was added to Versagel R1600 liquid (5 g), heated to 100° C. Full solubilisation was achieved with mixing within 10 minutes. The homogeneous mixture was spread on polyester sheet using a hand spreading block with a 760 micron slit height. The product was fully transparent with no visible particulates and was red-tinted.

Example 18

Preparation of Versagel R1600 Containing a Uniform Concentration of 2-(2,4-dimethylphenylamino)-3-methyl-6-diethylaminofluoran (0.5% w/w), a Black Colour-Former WinCon-15 powder (50 mg) was added to Versagel R1600 liquid (5 g), heated to 100° C. Full solubilisation was achieved with mixing within 10 minutes. The homogeneous mixture was spread on polyester sheet using a hand spreading block with a 760 micron slit height. The product was fully transparent with no visible particulates and was colourless.

Example 19

Preparation of Versagel R1600 Containing a Uniform Concentration of 3,3-bis(N-octyl-2-methyl indole)phthalide (0.5% w/w), a Red Colour-Former WinCon Red powder (50 mg) was added to Versagel R1600 liquid (5 g), heated to 100° C. Full solubilisation was achieved with mixing within 10 minutes. The homogeneous mixture was spread on polyester sheet using a hand spreading block with a 760 micron slit height. The product was fully transparent with no visible particulates and was colourless.

Example 20

Preparation of Versagel R1600 Containing a Uniform Concentration of 4,4'-[(1-methylethylidene)bis(4,1-phenyleneoxy-4,2-guinazolinediyl)]bis[N,N-diethyl]benzamine (0.5% w/w), a Yellow Colour-Former Pergascript Yellow I 3R powder (50 mg) was added to Versagel R1600 liquid (5 g), heated to 100° C. Full solubilisation was achieved with mixing within 10 minutes. The homogeneous mixture was spread on polyester sheet using a hand spreading block with a 760 micron slit height. The product was fully transparent with some visible particulates and was otherwise colourless.

Example 21

Demonstration of Colour-Forming Ability of Devices Produced in Examples 16-20

2×2 cm squares of each of the sheet materials produced in Examples 16-20 were cut by mechanical press. The polyester backing sheet was left in place for ease of handling. Each sample was placed, exposed Versagel side-down onto a sheet of Fuji Prescale C-Film. The colour intensity of each sample was recorded at the appropriate light absorbance wavelength over 6 minutes, during which strong colours were developed. The light absorbance was recorded using a UV-vis spectrometer with integrating sphere attachment (Avantes Avaspec 2048). The resulting light absorbances are represented graphically in FIG. 26.

This example demonstrates the rapid rate of colour development that can be achieved using a hydrocarbon gel as a delivery means for colour formers.

Example 22

Figure 1:
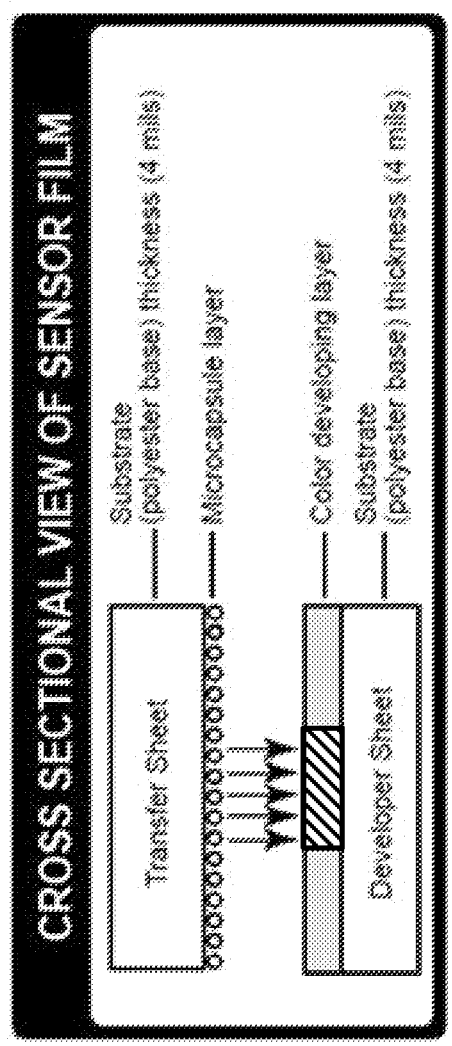
FIG. 1 shows an extract from the user instruction manual for a prior art product (Fuji), depicting the image-development process. In principle, this pressure recording film is similar in its operation and components to carbonless copy paper (CCP)
Figure 2:
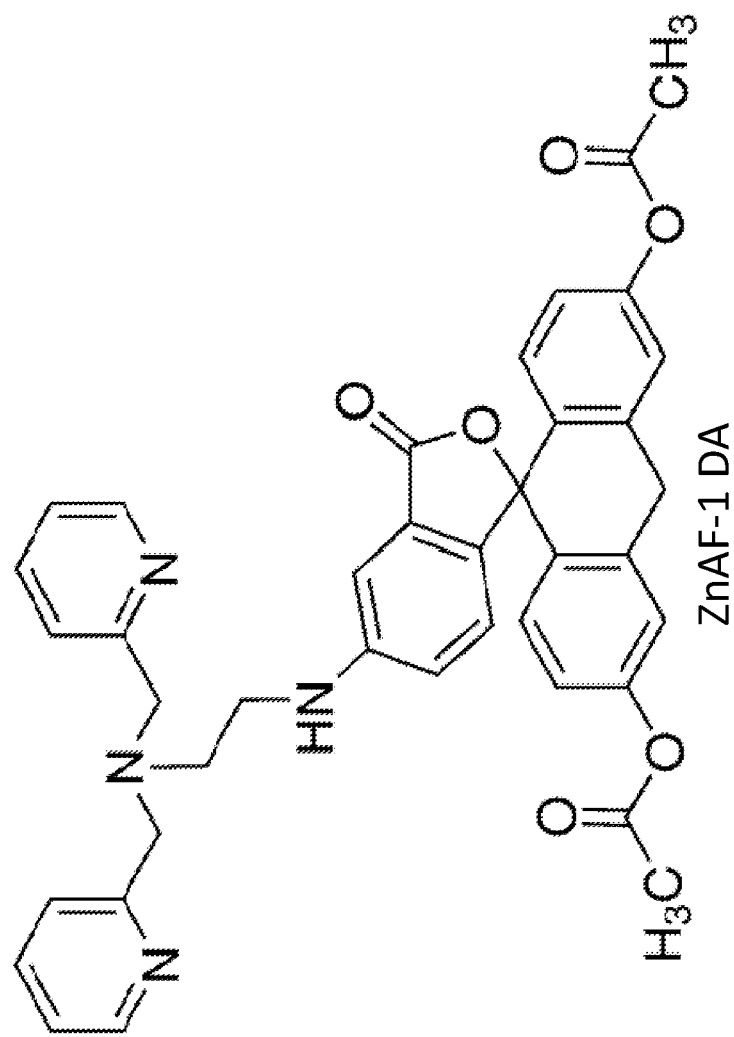
FIG. 2 illustrates the chemical structure of a colour forming material as used in certain embodiments of the present invention.
Figure 3:
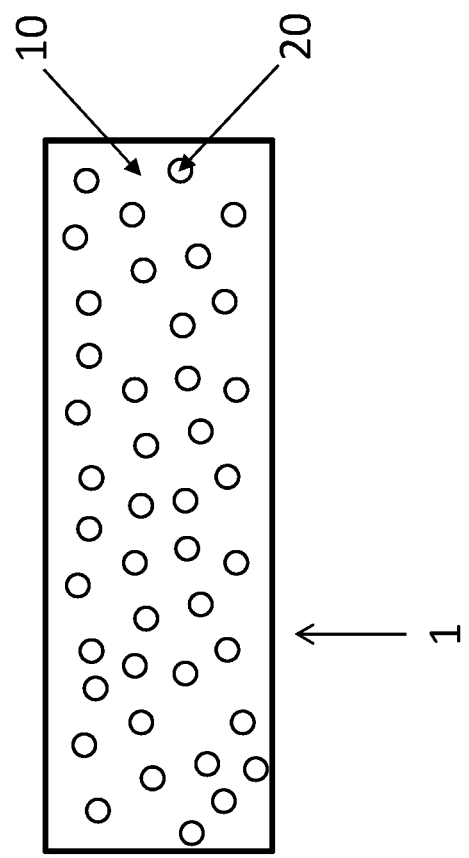
FIG. 3 illustrates a device (1) of certain embodiments of the invention comprising a first element (10) in which is dispersed a colour-forming material in its colourless state (20). Aptly, the first element is constructed of a solid material that allows the diffusion of the colour-forming material.
Figure 4:
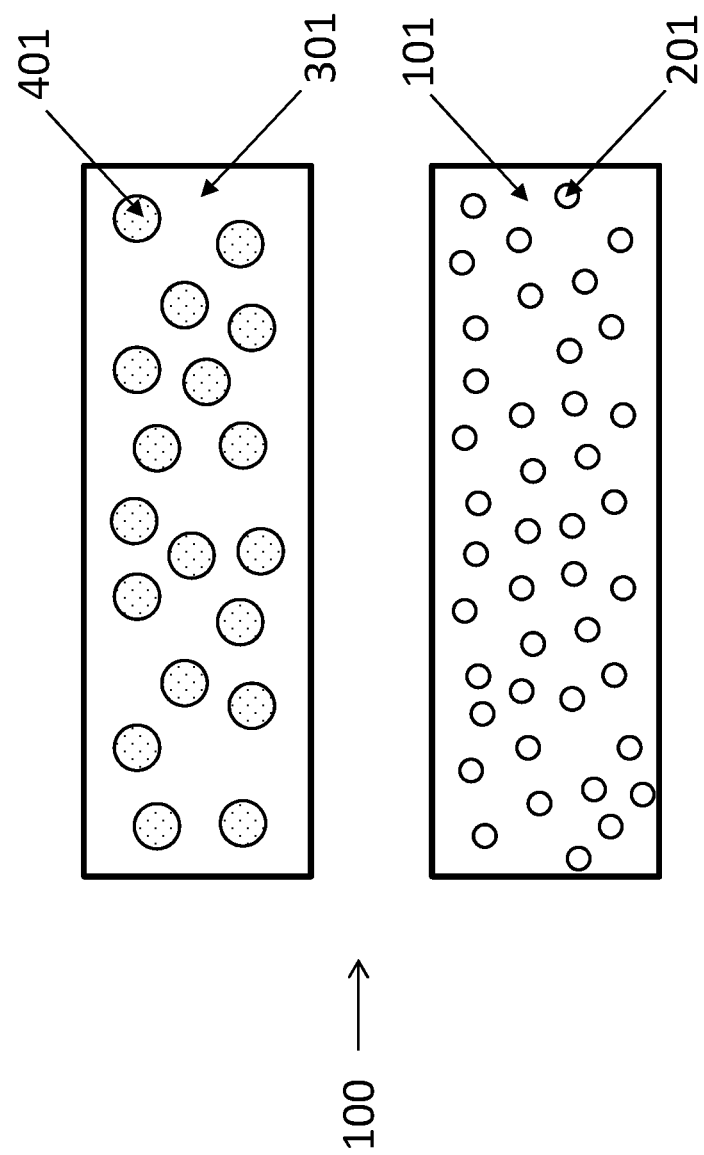
FIG. 4 illustrates a device (100) of certain embodiments of the invention comprising a first element (101) in which is dispersed a colour-forming material in its colourless state (201), and a second element (301) in which is dispersed a colour developer (401). The first element and second element are constructed of a solid material that allows the diffusion of the colour-forming material but not the colour developer.
Figure 5:
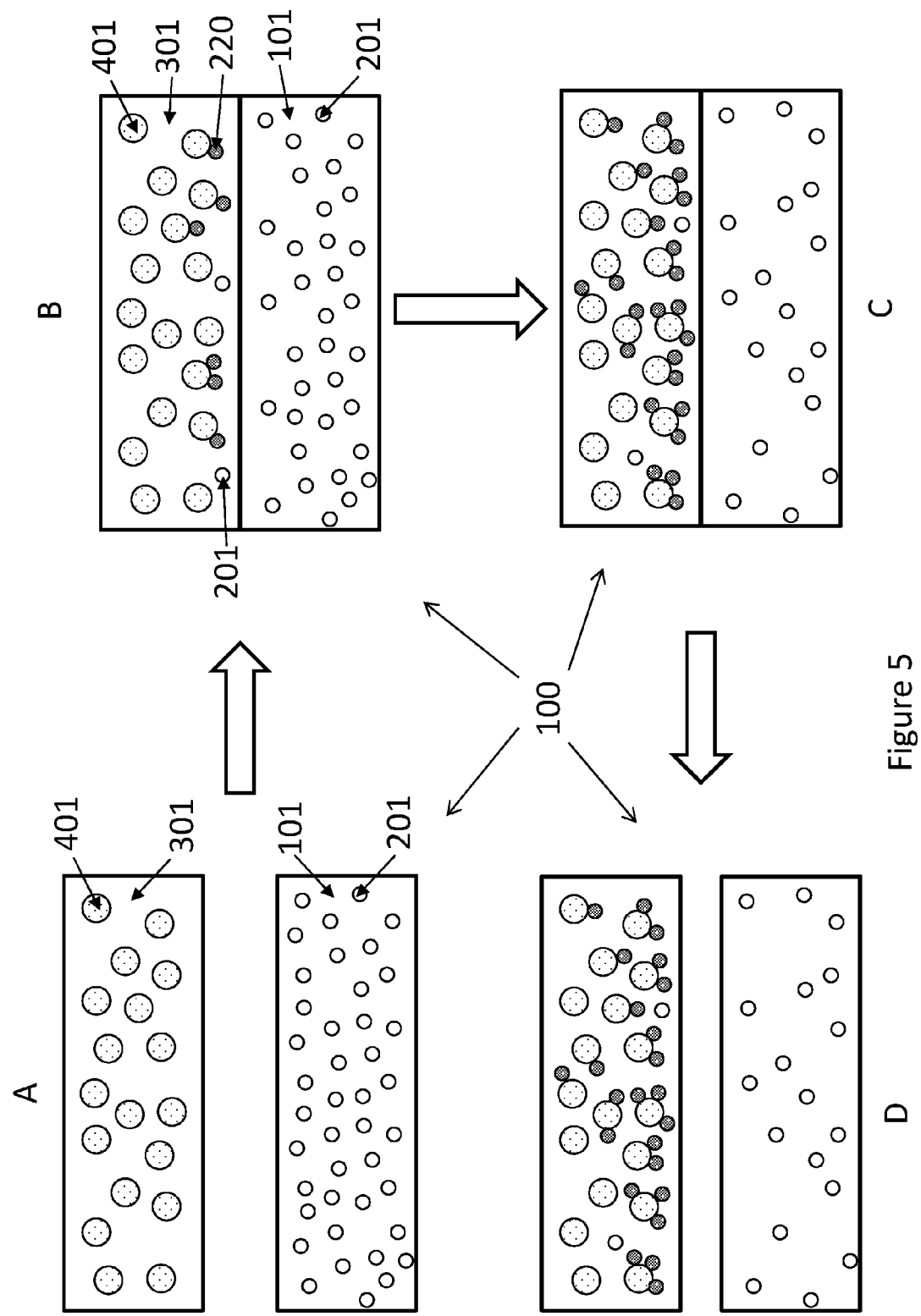
FIG. 5 is a schematic representation of the general operating principle of one embodiment of the invention.
Figure 6:
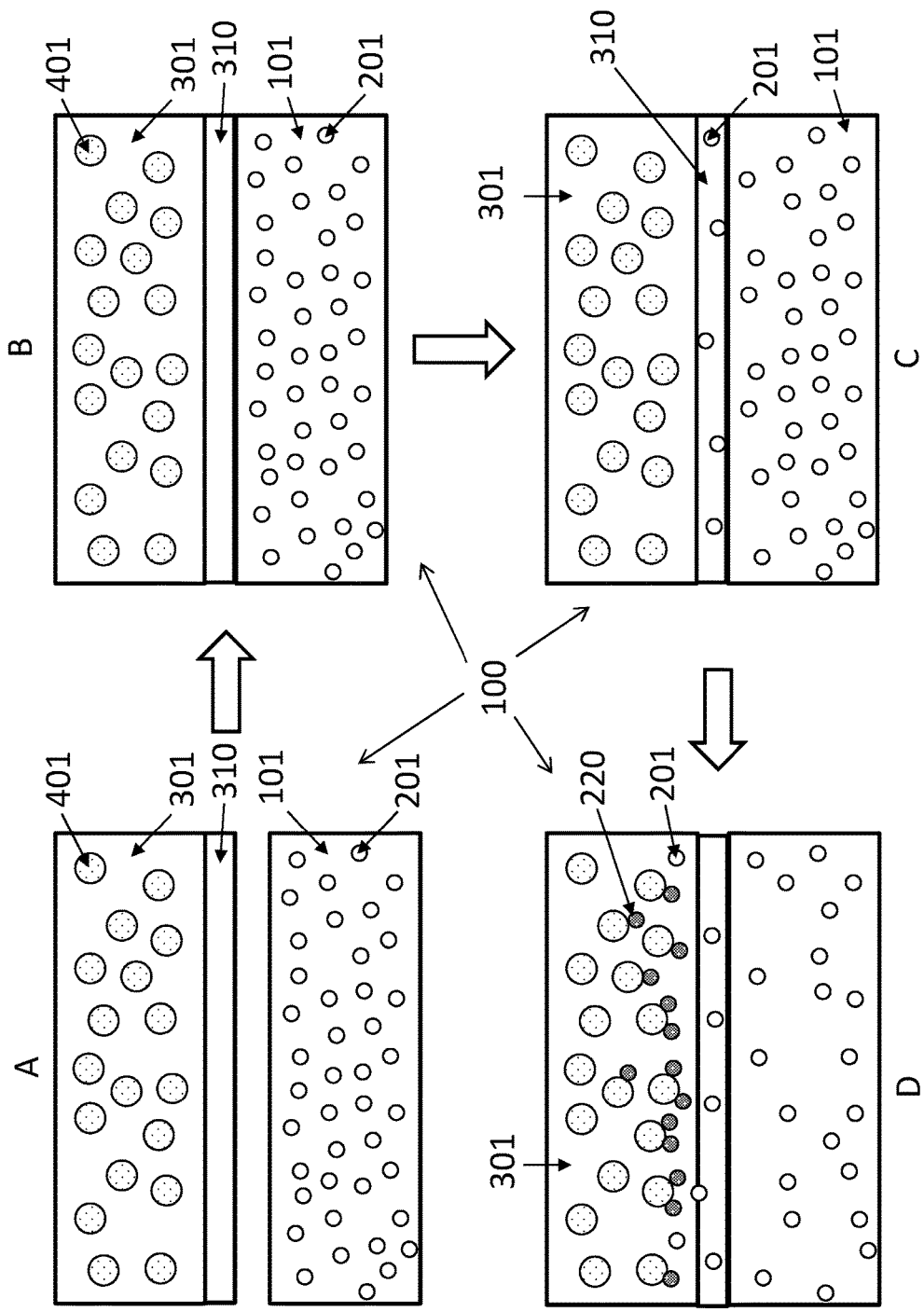
FIG. 6 is a schematic representation of an embodiment of the present invention.

Preparation of Colour Developer Layer Coated with a Versagel Barrier Layer for the Controlled Delay of Colour-Forming Response Time In some embodiments of this invention, it is desirable to indicate the duration of a contact time, for the indication of contact or pressure. In some of these cases it is also desirable for the device to not indicate contacts or pressures that occur below a specific duration threshold. FIG. 6 and its associated description describe such an arrangement and it is the purpose of this example to demonstrate this embodiment.

A sheet of Fuji Prescale C-Film (30×15 cm) was coated on its colour-developing face with a layer of Versagel R1600 using a spreading block. Several coat-thicknesses were generated. Samples of each material were cut to 2×2 cm squares and each material placed individually, face-to-face, against a 2×2 cm sample of the material produced in Example 19. The light absorbance of each sample combination was recorded at 538 nm over several seconds, minutes or hours, as appropriate and the time of initial light absorbance was also noted (this giving an approximate measure of diffusion time across the colour-former and colour-developer free layer).

The trend in light absorbance is shown in FIG. 27 for each sample. It can be concluded that the time required for colour development is increased in a predictable manner with increasing depth of barrier layer.

It could also be estimated that the maximum diffusion rate of this colour former (WinCon Red) through Versagel R1600 at 20° C. was approximately 50 um/min, consistent with an activation energy typical of diffusion-based indicators of 0-60 kJmol$^{-1}$ Example 23

Demonstration of Ability of a Device Components to Function in Water

The colour former material produced in Example 4 and the colour former material produced in Example 16 were immersed in water and individually brought into contact with the colour developer material produced in Example 11, itself immersed in water. Colour development occurred, as in air, on the colour-developer material, demonstrating that this technology is capable of operation in a liquid medium as well as air. This may have utility for use in liquid environments.

Example 24

Demonstration of Colour Development where the Second Element is Comprised Entirely of a Colour Developer The colour-former material produced in Example 4 and the colour-former material produced in Example 16 were individually brought into contact with an un-glazed ceramic surface made of porcelain. Colour development commenced on the surface of the ceramic within minutes and remained when the colour-forming materials were removed from the ceramic surface.

Example 25

Preparation of a Single-Part Silicone Elastomer Containing a Uniform Concentration of 3,3-bis(N-octyl-2-methyl indole)phthalide (0.5% w/w), a Red Colour-Former The material produced in Example 25 is similar to that produced in Example 4 but the silicone elastomer is formed from a commercially available single-part sealant of the type suitable for use in the home.

WinCon Red powder, 50 mg (Connect Chemicals GmbH) was added to Unibond Anti-Mould Sealant, 10 g (Henkel Ltd) and mixed by hand using a spatula until homogeneous distribution was achieved. The homogeneous mixture was spread on acetate sheet using a hand spreading block with a 760 micron slit height. The colour-former was substantially dissolved in the uncured prepolymer at this stage. The spread sheet was placed in an oven at 70° C. for 20 minutes to cure the silicone to an elastomeric solid of approximately 75 Shore OO hardness. The product was fully transparent with some visible particulates and had a red tint.

Example 26

Demonstration of Colour Development from a Colour-Former Material Prepared from a Single-Part Silicone Elastomer and Containing a Uniform Concentration of 3,3-bis(N-octyl-2-methyl indole) phthalide (0.5% w/w), a Red Colour-Former The material produced in Example 25 was placed in direct contact with the colour-developer material produced in Example 11. Colour development commenced on the surface of the colour-developer material within minutes and remained there when the components were separated.

Example 27

Demonstration of Temperature-Insensitivity of the Materials of this Invention Relative to the Time-Temperature Indicators (TTIs) of the Prior Art The material produced in Example 4 was placed in contact with a Fuji C-film and incubated at 15° C. Every 5 minutes for 60 minutes, the light absorbance of this sample was recorded at 538 nm. This experiment was repeated at incubation temperatures of 30° C. and 50° C. The results are shown in FIG. 28 and demonstrate that this combination of materials is substantially temperature insensitive (for example in comparison with time-temperature integrating devices of the prior art).

Example 28

Preparation of a Device for the Measurement of Intermittent Pressure

20×20 mm squares of the materials otherwise prepared as described in Examples 11 and 16 were positioned centrally, with edges aligned, and on opposing faces of an 30×30 mm square of monofilament woven with 100 apertures per square centimeter and an open area of >90%. A 30×30 mm square sheet of PET film of 12 micron thickness was placed centrally, with edges aligned, upon the remaining open face of each elastomer and 5 mm edge weld was applied to the full perimeter of the construction, trapping the elastomeric sheets in place centrally. FIG. 9 illustrates this process.

An adhesive coating was applied to one face of this construction, suitable for application to a human body.

Example 29

Preparation of Silicone Elastomer Containing a Uniform Concentration of Crystal Violet Lactone (0.5% w/w), a Blue Colour-Former Crystal violet lactone powder (50 mg) was added to Elastosil P7676 Part A liquid, 5 g (Wacker Chemie AG) and mixed by hand using a spatula until homogeneous distribution was achieved. The part-solubilisation of the crystal violet lactone could be observed by the greying of the liquid; full solubilisation was not achieved at this stage. To this homogeneous mixture was added Elastosil P7676 Part B liquid, 5 g (Wacker Chemie AG) and the components intimately mixed by hand using a spatula. Further solubilisation of the crystal violet lactone occurred. The homogeneous mixture was spread on acetate sheet using a hand spreading block with a 760 micron slit height. The crystal violet lactone was fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a very slight blue tint.

Example 30

Preparation of Silicone Elastomer Containing a Uniform Concentration of Crystal Violet Lactone (0.5% w/w), a Blue Colour-Former Crystal violet lactone powder (50 mg) was added to Elastosil P7600 Part A liquid, 5 g (Wacker Chemie AG) and mixed by hand using a spatula until homogeneous distribution was achieved. The part-solubilisation of the crystal violet lactone could be observed by the greying of the liquid; full solubilisation was not achieved at this stage. To this homogeneous mixture was added Elastosil P7600 Part B liquid, 5 g (Wacker Chemie AG) and the components intimately mixed by hand using a spatula. Further solubilisation of the crystal violet lactone occurred. The homogeneous mixture was spread on acetate sheet using a hand spreading block with a 760 micron slit height. The crystal violet lactone was fully dissolved in the uncured prepolymer at this stage. The spread sheet was placed in an oven at 70° C. for 20 minutes to cure the silicone to an elastomeric solid of approximately 30 Shore OO hardness. The product was fully transparent with no visible particulates and had a very slight blue tint.

Example 31

Description of a Method for Rapid Assessment of Pressure-Indicating Threshold in Certain Embodiments of this Invention Certain embodiments of the invention are concerned with the colour-indication of applied pressure duration above a defined pressure threshold. This pressure threshold may be in the range −1000 to +1000 mmHg relative to ambient pressure. Colour-indication occurs when the first and second element of a device come into contact and ceases when they are separated. Colour development occurs at a rate determined by the material and chemical properties of the hydrophobic material from which the first and second elements are constructed and the chemical properties of the colour-forming species. Frequently, colour development occurs at a speed that can be visualised by eye within minutes or hours. This rate may be too slow to be experimentally convenient, therefore it is desirable to easily visualise contact of the first and second elements in real-time (as increasing pressure is applied) without the need to wait for definitive colour development (which will follow). To this end, the experimental arrangement shown in FIG. 30 is set up.

The invention claimed is:
1. A device, comprising:
a first element comprising an elastomeric hydrophobic material and a colour-forming material dispersed in at least a portion of the elastomeric hydrophobic material; and
a second element comprising a colour developing material;
wherein the device is adapted to record one or more parameters selected from:
duration of application of a pressure applied to the device or portion thereof, wherein the pressure level is above or below a predetermined threshold value, and wherein the duration of application is continuous or non-continuous;
application of contact with the device;

duration of contact, a predetermined level of pressure, or both, wherein the duration of contact is continuous or non-continuous;

the distribution of application of a pressure to the device or portion thereof, wherein the pressure is above or below a predetermined threshold value;

distribution of contact with the device or a portion thereof; and application of a shear force, wherein the parameter is selected from direction, the shear force, or both.

2. The device according to claim 1, wherein the elastomeric hydrophobic material is capable of permitting diffusion of the colour-forming material through its structure and further wherein the elastomeric hydrophobic material has a hardness of between about 0 and 80 Shore 00.

3. The device according to claim 1, wherein the elastomeric hydrophobic material is a silicone-based elastomer.

4. The device according to claim 1, wherein the elastomeric hydrophobic material comprises an amount of the colour-forming material selected from: between about 0.01% and 20% w/w; and between about 0.1% and 10% w/w.

5. The device according to claim 1, wherein the colour forming material is substantially completely dissolved in the hydrophobic material.

6. The device according to claim 5, wherein the colour forming material is a colour forming chemical which is a molecular dispersion or partial molecular dispersion in the hydrophobic material.

7. The device according to claim 1, wherein the colour forming material is a phthalide-based leuco dye.

8. The device according to claim 7, wherein the phthalide-based leuco dye is selected from the group consisting of: crystal violet lactone, 6-diethylamino-3-methyl-2-phenylaminofluoran, 2-Anilino-6-dibutylamino-3-methylfluoran, 6-(N-ethyl, N-isopentylamino)-3-methyl-2-phenylaminofluoran, 2-(dibenzylamino)-6-(diethylamino)fluoran, 2-(2,4-dimethylphenylamino)-3-methyl-6-diethylaminofluoran, 3,3-bis(N-octyl-2-methyl indole)phthalide and 4,4'-[(1-methylethylidene)bis(4,1-phenyleneoxy-4,2-quinazolinediyl)]bis[N,N-diethyl]benzamine.

9. The device according to claim 1, wherein the second element is a solid-state element, wherein optionally the second element is an elastomeric hydrophobic material.

10. The device according to claim 9, wherein the colour developing material is substantially uniformly dispersed in at least a portion of the elastomeric hydrophobic material.

11. The device according to claim 10, wherein the elastomeric hydrophobic material of the second element is a silicone-based material.

12. The device according to claim 9, wherein the colour developing material is a particulate.

13. The device according to claim 12, wherein the colour developing material is selected from the group consisting of: a clay, a ceramic powder, an acid clay, montmorillonite clay, activated clay, alumina, silica, silica gel, aluminium sulphate, aluminium phosphate, attapulgite, bentonite, acid-activated bentonite, calcium stearate, kaolin, halloysite, zeolite, zinc chloride, zinc nitrate, lauryl gallate, gallic acid, maleic acid, malonic acid, succinic acid, bisphenol A, salicylic acid, sulfosalicylic acid, substituted salicylic acids, phenol and substituted phenols.

14. The device according to claim 1, wherein the first element is a sheet that is optionally flexible and the second element is a sheet that is optionally flexible.

15. The device according to claim 1, further comprising a third element located to maintain the first element and the second element in a non-associated state until a pressure greater than or less than a predetermined threshold value is applied to the device.

16. The device according to claim 15, wherein the third element is located between the first element and the second element.

17. The device according to claim 15, wherein the third element comprises one or more apertures.

18. A method of indicating the duration of application or removal of pressure, comprising locating a device according to claim 1 in a target location and detecting a colour change of the device.

19. A method of preventing or reducing pressure sore formation on a human or animal body, comprising locating a device according to claim 1 in a target location and detecting a colour change of the device.

20. The device according to claim 1, further comprising:
a first component comprising the first element; and
a second component comprising the second element;
wherein the first component and the second component are separable and are brought into contact in use.

21. The device according to claim 1, further comprising a single unitary component comprising the first element and the second element.

22. A system, comprising:
a first element comprising an elastomeric hydrophobic material and a colour-forming material dispersed in at least a portion of the elastomeric hydrophobic material; and
a second element comprising a colour-developing material
wherein the system is adapted to record one or more parameters selected from:
duration of application of a pressure applied to the device or portion thereof, wherein the pressure level is above or below a predetermined threshold value, and wherein the duration of application is continuous or non-continuous;
application of contact with the device;
duration of contact, a predetermined level of pressure, or both, wherein the duration of contact is continuous or non-continuous;
the distribution of application of a pressure to the device or portion thereof, wherein the pressure is above or below a predetermined threshold value;
distribution of contact with the device or a portion thereof; and
application of a shear force, wherein the parameter is selected from direction, the shear force, or both.

* * * * *